United States Patent
Olsson et al.

(10) Patent No.: US 10,359,368 B1
(45) Date of Patent: Jul. 23, 2019

(54) PIPE INSPECTION SYSTEM WITH JETTER PUSH-CABLE

(71) Applicant: SeeScan Inc., San Diego, CA (US)

(72) Inventors: Mark S. Olsson, La Jolla, CA (US); Eric M. Chapman, Lake Tapps, WA (US); Justin W. Taylor, Bend, OR (US); Matthew J. Thompson, San Jose, CA (US)

(73) Assignee: SeeScan, Inc., San Diego, CA (US)

( * ) Notice: Subject to any disclaimer, the term of this patent is extended or adjusted under 35 U.S.C. 154(b) by 0 days.

(21) Appl. No.: 15/728,410

(22) Filed: Oct. 9, 2017

Related U.S. Application Data

(63) Continuation of application No. 14/690,285, filed on Apr. 17, 2015, now Pat. No. 9,791,382, which is a continuation of application No. 13/073,919, filed on Mar. 28, 2011, now Pat. No. 9,468,954.

(60) Provisional application No. 61/318,122, filed on Mar. 26, 2010.

(51) Int. Cl.
| | |
|---|---|
| *G01N 21/954* | (2006.01) |
| *B05B 13/06* | (2006.01) |
| *B05B 1/14* | (2006.01) |
| *E03F 7/12* | (2006.01) |
| *H04N 5/225* | (2006.01) |
| *B08B 9/049* | (2006.01) |
| *B08B 9/043* | (2006.01) |
| *E03F 9/00* | (2006.01) |
| *F16L 101/30* | (2006.01) |
| *F16L 101/12* | (2006.01) |

(52) U.S. Cl.
CPC ............. *G01N 21/954* (2013.01); *B05B 1/14* (2013.01); *B05B 13/0627* (2013.01); *B05B 13/0636* (2013.01); *B08B 9/0433* (2013.01); *B08B 9/0495* (2013.01); *E03F 7/12* (2013.01); *E03F 9/00* (2013.01); *H04N 5/2258* (2013.01); *F16L 2101/12* (2013.01); *F16L 2101/30* (2013.01); *H04N 5/2252* (2013.01); *H04N 2005/2255* (2013.01)

(58) Field of Classification Search
None
See application file for complete search history.

(56) References Cited

U.S. PATENT DOCUMENTS

| | | |
|---|---|---|
| 3,370,599 A | 2/1968 | Ciaccio |
| 4,985,763 A | 1/1991 | Fraser |
| 5,018,545 A | 5/1991 | Wells |
| 5,571,977 A | 11/1996 | Kipp |
| 5,720,309 A | 2/1998 | Baziuk |

(Continued)

OTHER PUBLICATIONS

General Pipe Cleaners, "What's New? Drain-Rooter PH," Website, Mar. 16, 2010, McKees Rocks, PA, USA.

*Primary Examiner* — Eileen M Adams
(74) *Attorney, Agent, or Firm* — Steven C. Tietsworth, Esq.

(57) ABSTRACT

Pipe inspection systems including a push-cable, jetter, and camera assembly are disclosed. A jetter nozzle may be configured to spin and/or propel the camera head within a pipe or other cavity. A cutter line may be attached to the camera head to clean obstructions. A sonde may be coupled to a camera head to generate magnetic field signals for use with a buried utility locator to locate a pipe or other cavity into which the camera head is deployed.

20 Claims, 21 Drawing Sheets

(56) References Cited

U.S. PATENT DOCUMENTS

| | | | | |
|---|---|---|---|---|
| 5,862,561 | A | * | 1/1999 | Irwin .................. B08B 9/045 |
| | | | | 134/113 |
| 5,996,159 | A | | 12/1999 | Irwin |
| 6,857,158 | B1 | | 2/2005 | Hunter et al. |
| 7,040,331 | B2 | | 5/2006 | Garman et al. |
| 9,468,954 | B1 | * | 10/2016 | Olsson ................ B08B 9/0433 |
| 9,791,382 | B2 | * | 10/2017 | Olsson ................ G01N 21/954 |
| 2003/0201360 | A1 | * | 10/2003 | Hill .................... B65H 81/08 |
| | | | | 242/443 |
| 2005/0045747 | A1 | | 3/2005 | Hacquebord |
| 2005/0268940 | A1 | * | 12/2005 | Vohra .................. B08B 1/008 |
| | | | | 134/6 |
| 2007/0068434 | A1 | * | 3/2007 | Tsumiyama ......... B63B 35/731 |
| | | | | 114/55.53 |
| 2009/0236004 | A1 | * | 9/2009 | Jani .................... F61L 11/083 |
| | | | | 138/127 |
| 2010/0277617 | A1 | * | 11/2010 | Hollinger ............ H04N 5/2252 |
| | | | | 348/231.99 |

\* cited by examiner

PIPE INSPECTION SYSTEM WITH JETTER PUSH-CABLE

CROSS-REFERENCE TO RELATED APPLICATIONS

This application is a continuation of and claims priority to co-pending U.S. Utility application Ser. No. 14/690,285, entitled PIPE INSPECTION SYSTEM WITH JETTER PUSH-CABLE, filed Apr. 17, 2015, which is a continuation of and claims priority to U.S. Utility patent application Ser. No. 13/073,919, now U.S. Pat. No. 9,468,954, entitled PIPE INSPECTION SYSTEM WITH JETTER PUSH-CABLE, filed on Mar. 28, 2011, which claims priority under 35 U.S.C. § 119(e) to U.S. Provisional Patent Application Ser. No. 61/318,122, entitled PIPE INSPECTION SYSTEM WITH JETTER PUSH-CABLE, filed on Mar. 26, 2010. The content of these applications is incorporated by reference herein in its entirety for all purposes.

This application is also related to U.S. patent application Ser. No. 12/371,540, now U.S. Pat. No. 8,289,385, entitled HIGH PERFORMANCE PIPE INSPECTION SYSTEM filed on Feb. 13, 2009, and to U.S. patent application Ser. No. 11/679,092, entitled LIGHTWEIGHT SEWER CABLE, filed on Feb. 26, 2007. The content of these applications is hereby incorporated by reference herein in its entirety for all purposes.

FIELD OF THE INVENTION

This invention relates generally to apparatus and systems for inspecting and cleaning the interior of pipes and other conduits or voids. More specifically, but not exclusively, this invention relates to apparatus and systems for clearing obstructions in pipes using pressurized fluid jetting, as well as providing imaging within pipes to facilitate inspection and cleaning.

BACKGROUND

Pipes are often prone to obstructions through a variety of mechanical, structural, and/or environmental factors such as structural damage, invasion by tree roots and/or other vegetation, other blockages, build-up and corrosion, as well as other blockages. Such factors are likely to influence the strategy employed for clearing such obstructions.

Devices and methods for visualizing the interior of a pipe are known in the art. For example, video pipe inspection systems have been developed that include a video camera head at the end of a cable that is manually forced down the pipe to display the pipe interior on a video display. The pipe inspection is commonly recorded using a video recorder (VCR) or digital video recorder (DVR). Current pipe clearing systems, however, are limited in their ability to deploy high pressure fluid to clear obstructions. Further, current systems are limited in their ability to combine imaging and/or other features in conjunction with high pressure fluid obstruction removal. Accordingly, there is a need in the art to provide improved apparatus and systems for facilitating obstruction removal and/or providing associated imaging.

SUMMARY

The present invention relates generally to pressurized fluid cleaning systems. For example, in one aspect, a camera assembly having one or more camera and/or light source elements may be mounted on a segment of a push-cable to observe a work area. For example, the camera and light source elements may be used in conjunction with a remote monitor, such as in proximity to an operator, to examine the pipe or other cavity, display the work area to be cleaned, and/or observe the cleaning process. The camera and/or light source elements may be automatically controlled and/or manually controlled by the operator. For example, Automatic control may be used to provide an image or video signal from one or more of the camera elements based on an orientation of the push-cable within the pipe or cavity. Control signals may be provided from a sensor such as an accelerometer.

Manual control may be used to allow an operator to select one or more of the camera elements for viewing the interior of the pipe or other cavity, such as by a switch, button, or other user input mechanism. Images or video from the camera elements may be multiplexed to provide multiple view of the interior of the pipe or other cavity. A fetter nozzle may be configured to be interchangeably coupled to the push-cable. For example, nozzles may be configured to control the direction or flow rate of the pressurized fluid, thereby adapting fluid output to use in varied applications. For example, jetted fluid may be used to deploy the push-cable and attached camera head within the pipe and/or to spin the nozzle or other elements of the push-cable to clear obstructions. The push-cable may be configured to accept commercially provided nozzles or other customized or proprietary nozzles.

In another aspect, a removable extender may be used to connect the nozzle to the push-cable. The rigidity and length of the removable extender may be configured in different ways depending on a particular application.

In another aspect, the nozzle may be equipped with cutting strands, such as flexible cutters, and/or with blades or other cutting elements capable of rotating as a result from the force of the fluid expelled from the nozzle. For example, as the push-cable is fed to the work area, such as at the location of a blockage within a clogged pipe, the flexible cutting strands and/or blades may be used to remove the blockage.

Various additional aspects, features, and functions are described below in conjunction with the appended Drawings.

BRIEF DESCRIPTION OF THE DRAWINGS

The present application may be more fully appreciated in connection with the following detailed description taken in conjunction with the accompanying drawings, wherein.

DETAILED DESCRIPTION OF EMBODIMENTS

Figure 1:
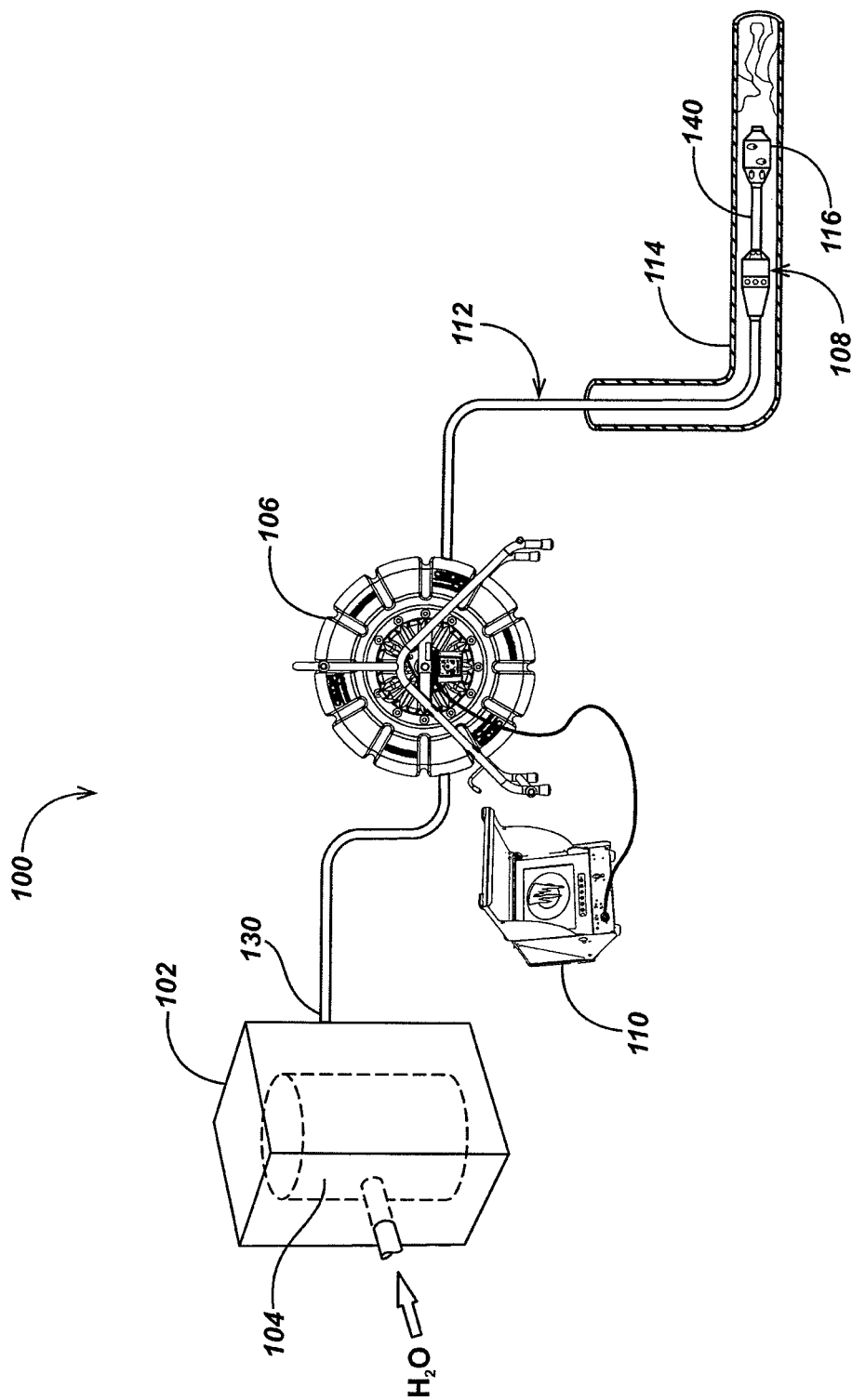
FIG. 1 is a diagrammatic illustration of an embodiment of a pipe inspection and jetting system.

The following exemplary embodiments are provided for the purpose of illustrating examples of various aspects, details, and functions of the present invention; however, the described embodiments are not intended to be in any way limiting. It will be apparent to one of ordinary skill in the art that various aspects may be implemented in other embodiments within the spirit and scope of the present invention.

This application is related by common authorship and field of application to U.S. Pat. No. 5,939,679, issued Aug. 17, 1999, entitled VIDEO PUSH CABLE, and to U.S. patent application Ser. No. 11/679,092 Feb. 26, 2007, Olsson, entitled Lightweight Sewer Cable, both of which are hereby incorporated by reference herein in their entirety.

The present invention relates generally to apparatus, systems, and associated methods for inspecting and cleaning the interior of pipes and other conduits or voids. More specifically, but not exclusively, this invention relates to apparatus and systems for clearing obstructions in pipes using pressurized fluid jetting and/or additional cutting elements, as well as providing imaging within pipes to facilitate inspection and cleaning.

For example, in one aspect, the invention relates to a cable apparatus for pressurized pipe cleaning. The apparatus may include, for example, a push-cable structure. The push-cable structure may include a hose element having a central channel configured for transmitting fluid under pressure through the push-cable structure. The apparatus may further include a stiffening structure, which may be helically wrapped around the hose to provide rigidity to the push-cable structure. The apparatus may further include a jetter nozzle. The jetter nozzle may be coupled to a distal end of the push-cable structure, and configured to control a flow of the pressurized fluid from the distal end of the push-cable.

The hose element may be made, for example, from a thermoplastic material. The push-cable structure may further include a reinforcing braid disposed around the hose. The stiffening structure may include a plurality of rods. The rods may be fiberglass rods. The rods may be metallic rods. The rods may be made from a composite material, such as carbon fiber and resin.

The cable apparatus may further include, for example, one or more drain wires distributed among the plurality of rods. The cable apparatus may further include one or more conductive wires distributed among the plurality of rods. The cable apparatus may further include a copper foil element disposed around the rods and the conductive wires to providing electrical shielding.

The cable apparatus may further include, for example, a camera assembly having a plurality of camera elements. The camera assembly may be an annular configuration. The camera assembly may be disposed around the central channel. The camera assembly may include a hose connector mechanism at a first end and a nozzle connector mechanism at a second end to facilitate coupling to the push-cable and/or nozzle. The camera assembly may be an annular camera assembly comprising three camera elements disposed equidistantly around the central channel. The plurality of camera elements may comprise imaging sensors. The imaging sensor may be configured to provide still images and/or video, and/or audio signals.

The cable apparatus may further include, fore example, one or more lighting elements. The lighting elements may be disposed in the camera assembly. The one or more lighting elements may be light emitting diodes (LEDs) or other lighting elements.

The cable apparatus may further include, for example, a position sensing device. The position sensing device may be an accelerometer. The accelerometer may be a 2 or 3 axis accelerometer. The position sensing device may be disposed in the camera assembly.

The cable apparatus may further include, for example, a camera element switching circuit. The camera element switching circuit may include electronic components on a circuit board or other substrate configured to receive outputs from the camera elements and select one or more outputs the plurality of camera elements. A particular camera element output may be selected to provide an orientation adjusted camera output. The orientation adjusted camera output may be selected based on information provided from the position sensing device. The orientation adjusted output may be provided to a display device, which may be in proximity to an operator.

The cable apparatus may further include, for example, an operator controlled switching circuit. The operator controlled switching circuit may be integral with or separate from the camera element switching circuit. The operator controlled switching circuit may be configured to select, responsive to an operator provided input, an output from one of the plurality of camera elements so as to provide an operator selected camera output. The operator selected camera output may be provided to a display device, which may be in proximity to an operator.

The cable apparatus may further include, for example, a multiplexer circuit. The multiplexer circuit may be integral with or separate from one or both of the camera element and operator switching circuits. The multiplexer circuit may be configured to multiplex ones of outputs from the plurality of camera elements to provide a multiplexed camera output. The multiplexed camera output may be provided to a display device, which may be in proximity to an operator.

The cable apparatus may further include, for example, an extender element coupled between the distal end of the push-cable structure and the jetter nozzle. The cable apparatus may further include one or a plurality of spring stiffeners configured to control the rigidity of sections of the camera assembly and extender. The cable apparatus may further include one or more spring stiffeners configured to control the rigidity of the push-cable apparatus. The spring stiffeners may be disposed on one or more segments of the push-cable apparatus.

The jetter nozzle may include one or a plurality of orifices. One or more orifices may be configured at a predefined orientation in the jetter nozzle so as to spin the jetter nozzle responsive to jetting of the pressurized fluid. One or more orifices may be configured at a predefined orientation in the jetter nozzle so as to propel the jetter nozzle and push-cable within a pipe or cavity being cleaned. One or more orifices may be configured at a predefined orientation in the jetter nozzle so as to clear debris or build up within a pipe or cavity being cleaned.

The cable apparatus may further include, for example, a cutting element. The cutting element may be a cutter line assembly. One or more orifices may be configured at a predefined orientation in the jetter nozzle and/or cutting element so as to rotate a cutter line within a pipe or cavity being cleaned. The cable apparatus may further include a cutter blade attachment assembly. The cutter blade attachment assembly may be configured to couple one or more cutter blades to the jetter nozzle and/or cutter line assembly.

The cable apparatus may further include, for example, a plurality of spring stiffeners disposed about the camera assembly to control the rigidity of sections of the camera assembly and extender.

The cable apparatus may further include, for example, a sonde element. The sonde element may be coupled to the cable apparatus and may be configured for locating a buried object.

In another aspect, the present invention relates to a system for pressurized fluid cleaning of a pipe or other cavity. The system may include, for example, A pump unit, a fluid storage unit coupled to the pump unit, and a push-cable. The push-cable may include a hose having a central channel configured for transmitting fluid under pressure through the push-cable structure. The push-cable may further include a stiffening structure helically wrapped around the hose to provide rigidity to the push-cable structure. The system may further include a jetter nozzle coupled to a distal end of the push-cable. The jetter nozzle may be configured to control a flow of the pressurized fluid from the distal end of the push-cable to facilitate cleaning of a pipe being inspected.

The system may further include, for example, a cutter element disposed adjacent to the distal end of the push-cable. The system may further include, for example, a camera assembly. The camera assembly may include one or more camera elements and one or more lighting elements. The system may further include one or more displays. The displays may be configured to receive images or video signals from the one or more camera elements. The system may further include one or more control elements for controlling the camera elements and/or lighting elements. The camera elements may be controlled to provide a selected image from ones of a plurality of the camera elements based on, for example, an orientation of the ones of camera elements. The system may further include an orientation sensing elements, such as a three-axis accelerometer. The sensing element may be used to provide an orientation signal to a switching circuit, which may be configured to switch an output from ones of a plurality of the camera elements for display on the displays.

In another aspect, the present invention relates to a method of clearing a pipe obstruction using an apparatus and/or system such as described previously. The method may include, for example, deploying a push cable in an obstructed cavity, wherein the push cable includes a push-cable structure including a hose having a central channel configured for transmitting fluid under pressure through the push-cable structure, a stiffening structure helically wrapped around the hose to provide rigidity to the push-cable structure, and a jetter nozzle coupled to a distal end of the push-cable structure, The jetter nozzle may be configured to control a flow of the pressurized fluid from the distal end of the push-cable. The pressurized fluid may be provided to the push cable from a tank and/or pump. The pressurized fluid may be provided from a distal end of the push-cable to control movement of the nozzle and/or clearance of an obstruction.

Various additional aspects, features, and functions are described below in conjunction with the embodiments illustrated in FIGS. 1 through 21 of the appended Drawings.

It is noted that as used herein, the term, "exemplary" means "serving as an example, instance, or illustration." Any aspect, detail, function, implementation, and/or embodiment described herein as "exemplary" is not necessarily to be construed as preferred or advantageous over other aspects and/or embodiments.

Some video pipe inspection systems have included a semi-rigid push-cable connecting a camera head. The push-cable is stored on a reel and can be manually pushed to move the camera head down the pipe. However, conventional push-cables do not have a channel in place to allow jetting high-pressure fluid. Some devices for cleaning pipes use hoses with jetter heads. Motorized pipe cleaning devices typically use a motor-driven rotating head equipped with cutter blades or brushes. However, such devices have a number of deficiencies. For example, they do not typically permit visualization of the pipe's interior while cleaning, and are difficult to transport to an inspection and/or cleaning site. The embodiments described below illustrated various aspect, features, configurations, and functions that may be used to address these as well as other deficiencies in current systems.

FIG. 1 illustrates a pipe inspection and jetting system 100 in accordance with various aspects of the present invention. System 100 may include a pump unit 102 for providing pressurized fluid and a heater unit 104 which may optionally be used to heat the fluid. These may be further combined with an injection system (not shown) for adding surfactants and/or other chemicals to the fluid.

A cable reel 106 may functionally connect between a camera assembly 108, and a monitor or other display device 110. A jetter push-cable 112, which may be stored and fed from the cable reel 106, may be used to provide pressurized fluid from pump unit 102 to a jetter nozzle 116. Push-cable 112 may also be used to couple signals from the camera assembly 108 to the display 110 and/or provide electrical power to camera assembly 108 from a power source (not shown). The camera assembly may be in an annular configuration around and/or integral with the push-cable 112.

The cable reel 106 may be configured with a combined rotating electrical slip ring and fluid swivel joint (not illustrated). Water or other fluids provided under pressure from pump 102 may be optionally heated and then sent through jetter push-cable 112 from a proximal end 130 to a distal end 140. Push-cable 112 may be manually moved down a pipe 114 by the operator to the location of an obstruction in a pipe or other cavity 114.

The camera assembly 108 may be seated around or within the exterior of the jetter push-cable 112. The pressurized fluid passes through jetter push-cable 112 and exits jetter nozzle 116 to clear build-up, roots, and/or other obstructions or blockages found in pipe or other cavity 114. Pressurized fluid may be further used to facilitate deployment of the push-cable 112, camera assembly 108, and jetter nozzle 106 within pipe 114, and/or provide other functions, such as spinning jetter nozzle 116 as further described subsequently herein.

FIGS. 2 through 21 illustrate details of embodiments of pipe inspection and jetting apparatus and systems in accordance with various aspects of the present invention, which may correspond with details and/or components of system 100 of FIG. 1, as well as example interior constructions and features thereof.

Figure 2:
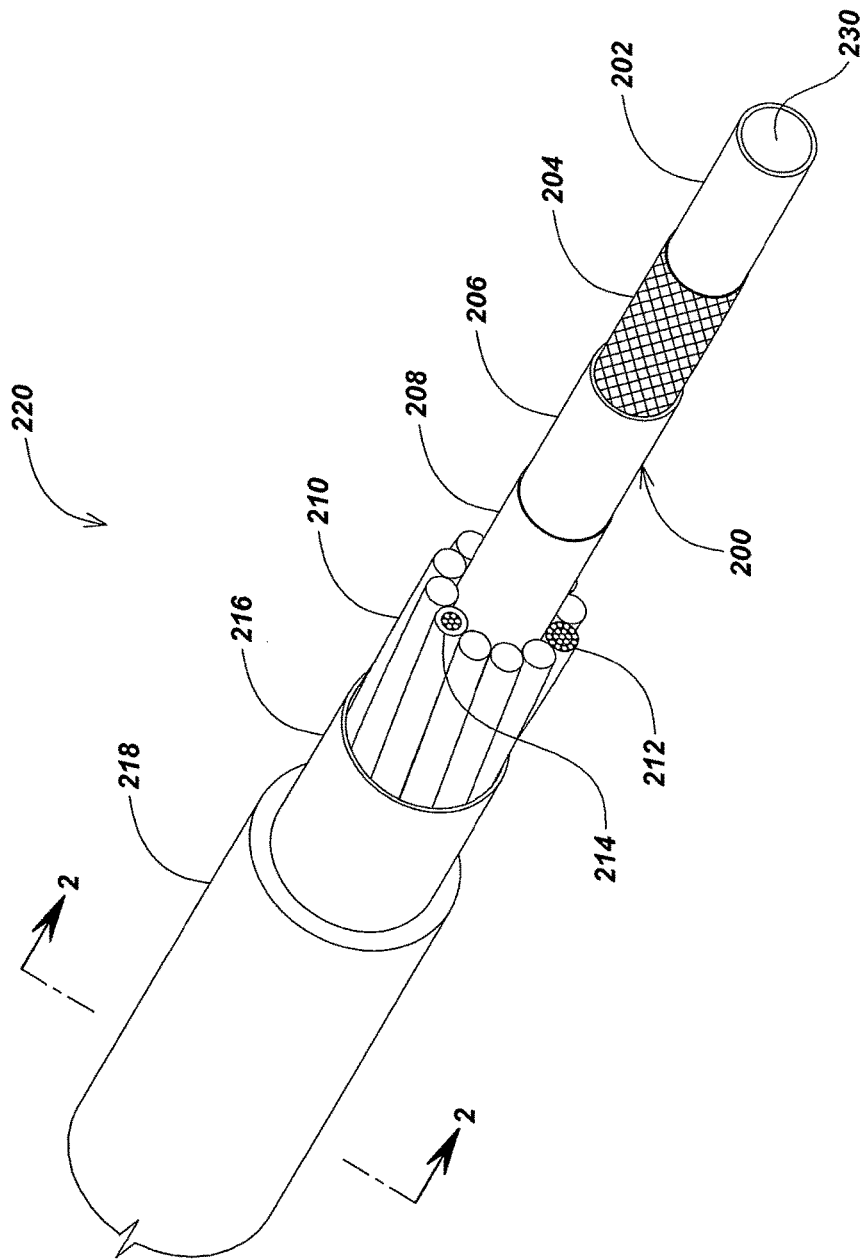
FIG. 2 is an enlarged fragmentary isometric view of an embodiment of a jetter push-cable.

Turning to FIG. 2, a perspective view illustrates details of an embodiment of a jetter push-cable 220, which may correspond to the jetter push-cable 112 of FIG. 1. Push-cable 220 may be used in the pipe inspection and jetting system 100 as shown in FIG. 1. A hose 220, such as a thermoplastic hose, may be built of a seamless inner core 202 with a central channel 230 to carry pressurized fluid, and may be surrounded by a high-tensile reinforcing braid 204, as well as a cover 206, such as a thin thermoplastic cover. The hose 200 may be a medium- or high-pressure hose such as, for example, the Piranha Series 201 hoses. A layer of low-friction tape 208, such as Teflon® tape, may optionally surround the hose 200.

Figure 3:
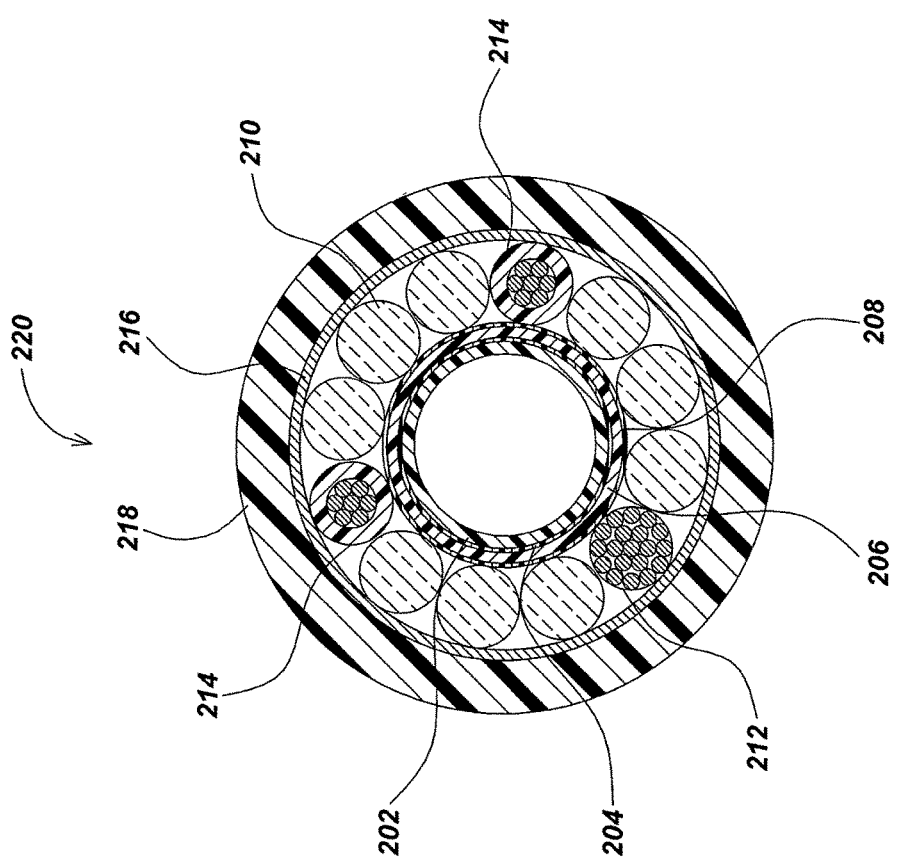
FIG. 3 is an end-view schematic of the embodiment of a jetter push-cable shown in FIG. 2.

A series of thin (1 mm in an exemplary embodiment) rods 210, which may be made of fiberglass and/or other lightweight high strength materials, may be wound helically around the hose 200. A drain wire 212, and/or a series of one or more conductive wires 214, may be distributed among the rods 210 to carry power and/or signals. The conductive wires 214 may individually be contained in jackets as shown in FIG. 3. A layer of copper foil 216 may optionally surround the rods 210, the drain wire 212, and/or the conductive wires 214 to act as electrical shielding. When the copper foil 216 is used, drain wire 212 may be used as an electrical drain. A jacket 218, such as a nylon jacket, may be used as the outermost layer of the jetter push-cable 112 to provide durability.

Turning to FIG. 3, components of jetter push-cable 220 of FIG. 2 are illustrated from an end or cross-sectional view. The jetter push-cable 220, which may correspond with one or more cable embodiments as disclosed in U.S. patent application Ser. No. 12/371,540 (incorporated by reference herein), may be combined with apparatus to transmit fluid under medium to high pressure (for example, 3500 p.s.i.). In an exemplary embodiment, camera assembly 108 may be mounted in the middle of a segment of the jetter push-cable 220 (in an embodiment where the push-cable is configured in segments) or hose 200 as shown in FIG. 2, rather than at the distal end of the push-cable.

Figure 4:
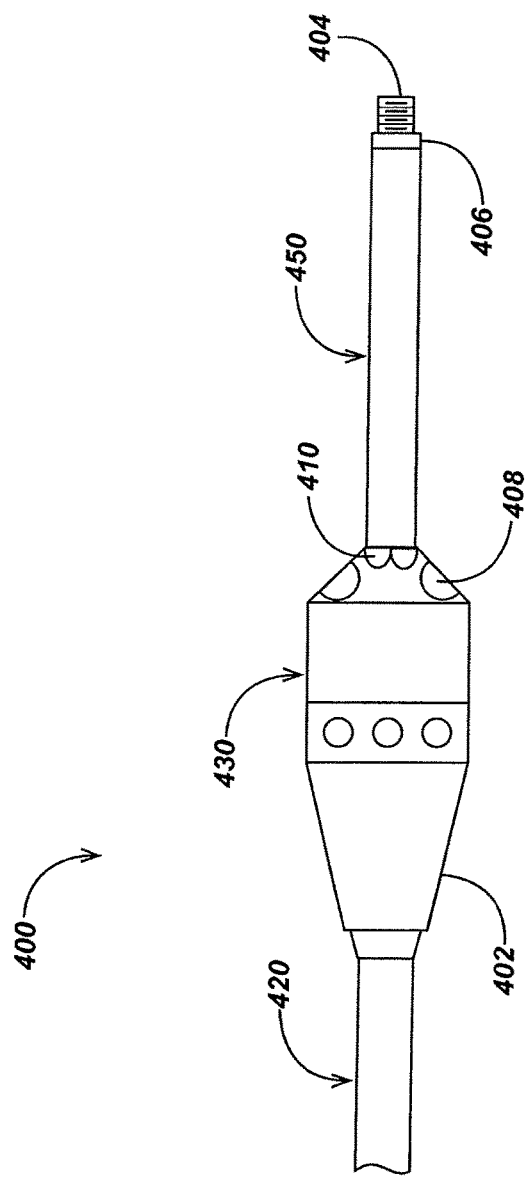
FIG. 4 is a side view of an embodiment of an effector end with a camera assembly.

FIG. 4 illustrates an embodiment of an effector end 400 of a push-cable 420. Push-cable 420 may correspond with push-cable 112 of FIG. 1 and/or push-cable 220 of FIG. 2. A camera assembly 430, which may correspond with camera assembly 108 of FIG. 1, may be mounted on or within a segment of the jetter push-cable 420 as shown. The camera assembly may be in an annular configuration mounted on or within the push-cable. For example, camera assembly 430 may be formed with a central circular opening so that a hose element 450, which may correspond with hose 200 of FIG. 2, may pass through the center of camera assembly 430.

Elements of the embodiment illustrated in FIG. 2, such as the low-friction tape 208, rods 210, drain wire 212, conductive wires 214, copper foil 216, and/or the jacket 218, may extend to an adaptor 402 connecting to the back of the camera assembly 430. The hose 450 may terminate in a coupler end 404 attached by a circular crimp 406 or other connection mechanism. An array of camera elements 408 and/or one or more light elements 410, such as LEDs, may be disposed onto or in the front face of camera assembly 430.

Figure 5:
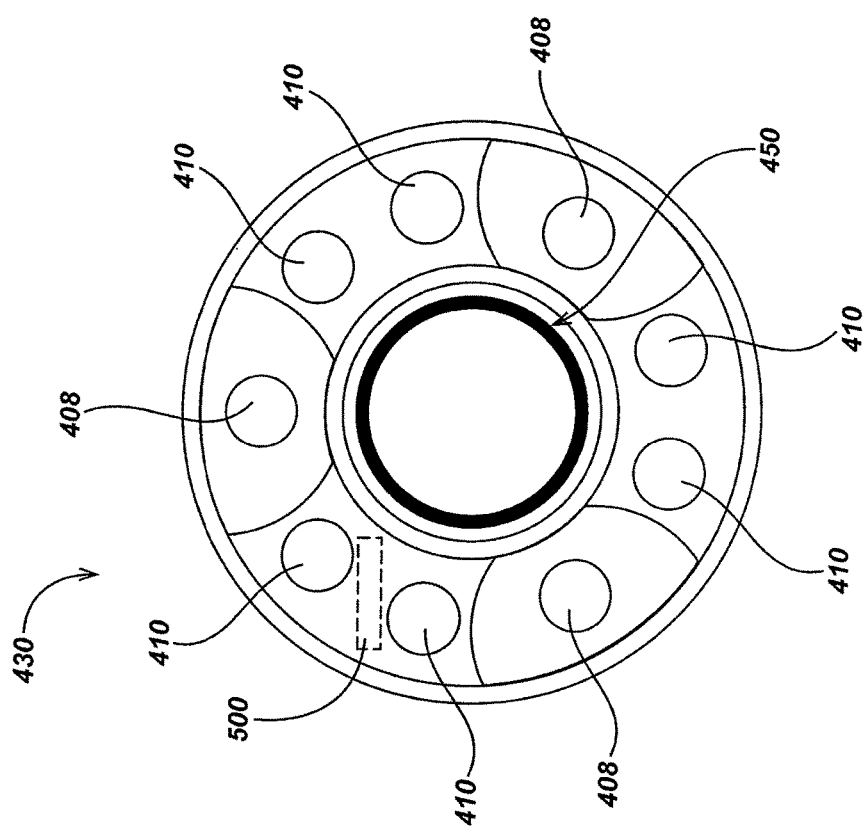
FIG. 5 is an end view of an embodiment of the annular camera assembly shown in FIG. 4.

FIG. 5 illustrates a cross-sectional view of the camera assembly embodiment 430 of FIG. 4, which may correspond with camera assembly 108 as shown in FIG. 1. In an exemplary embodiment, three camera elements 408, which may be small cameras, may be used. Other numbers and/or configuration of camera elements may be used in alternate embodiments. Camera elements 408 may be located equidistantly around the perimeter of the face of camera assembly 430. Between the camera elements 408, one or more light elements 410, which may be LEDs, may be disposed.

Hose 450, which may correspond to hose 200 as shown in FIG. 2, may be configured to protrude centrally through camera assembly 430. Within the body of the camera assembly 430, an orientation sensing device 500, such as a three-axis accelerometer, may be installed to provide a signal corresponding to an orientation of the camera elements 408. In some embodiments, input from sensing device 500 may be used by a switching circuit element (not shown) to selectively switch an output signal provided to a display, such as display element 110 as shown in FIG. 1, so that outputs from one or more particular camera elements 408 are shown on the display. For example, an accelerometer may provide an orientation signal to the switching circuit to provide an output from the uppermost one of the camera elements 408 to the display. In some embodiments, the switching circuit may be configured to receive a control input provided by a user so as to allow for manual selection of outputs from one or more of camera elements 408 for provision to the display. In some embodiments, images or video frames from each of the camera elements 408 may be multiplexed in the switching circuit, and the choice of displayed images or video frames controlled by software, or all displayed simultaneously or sequentially on the display.

Figure 6:
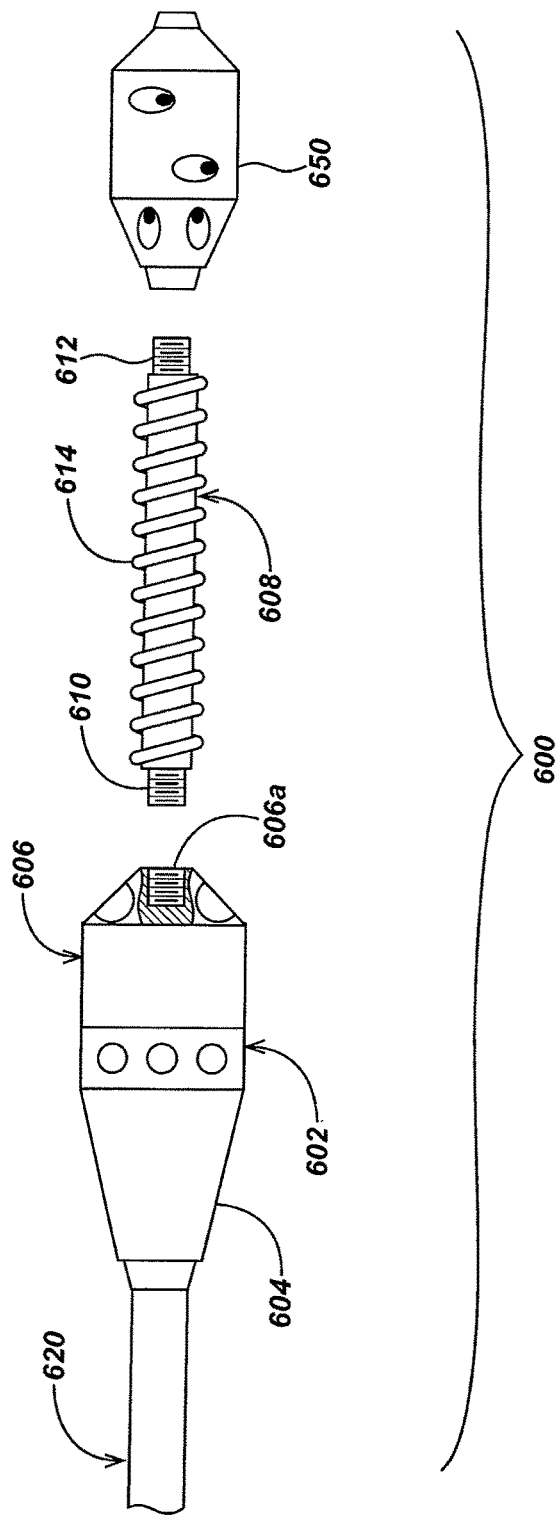
FIG. 6 is a side view of an embodiment of an end assembly.

FIG. 6 illustrates an alternative embodiment of an effector end 600 that may be coupled to a jetter nozzle 650, which may correspond with jetter nozzle 116 as shown in FIG. 1. A jetter push-cable 620, which may correspond to the jetter push-cable 112 as shown in FIG. 1, may be secured to a hose fitting camera assembly 602, with an adaptor 604, which may be secured to a camera head 606. A coupler 606a may be formed on the camera head 606 which may connect to an extender 608. In one embodiment of the effector end 600, the coupler 606a may be threaded. In other embodiments, other connection mechanisms, such as quick-disconnect couplings, may be used. For example, the extender 608 may be detachable, and may include a camera-side coupler 610 and a nozzle-side coupler 612. The camera-side coupler 610 may connect to the coupler 606a of the camera head 606 and the nozzle-side coupler 612 may connect to the jetter nozzle 650. Such an embodiment offers the advantage of using extenders of varying lengths and degrees of stiffness, depending on the requirements of the specific application.

In some embodiments, a spring stiffener 614, which may be optionally removable, may be included as shown in FIG. 6. The spring stiffener 614 may be secured around the extender 608 and anchored at its ends. Providing an optional means for increasing the stiffness of the extender 608 when deployed may be advantageous when the jetter push-cable 620 is used with forward-oriented jets, which may typically add back-pressure on the jetter push-cable 620 and the extender 608. The spring stiffener 614 may similarly be implemented with other configurations. For example, a continuous length of hose elements, such as shown in FIGS. 2, 4, and 5 may be used, rather than extender 608.

Figure 7:
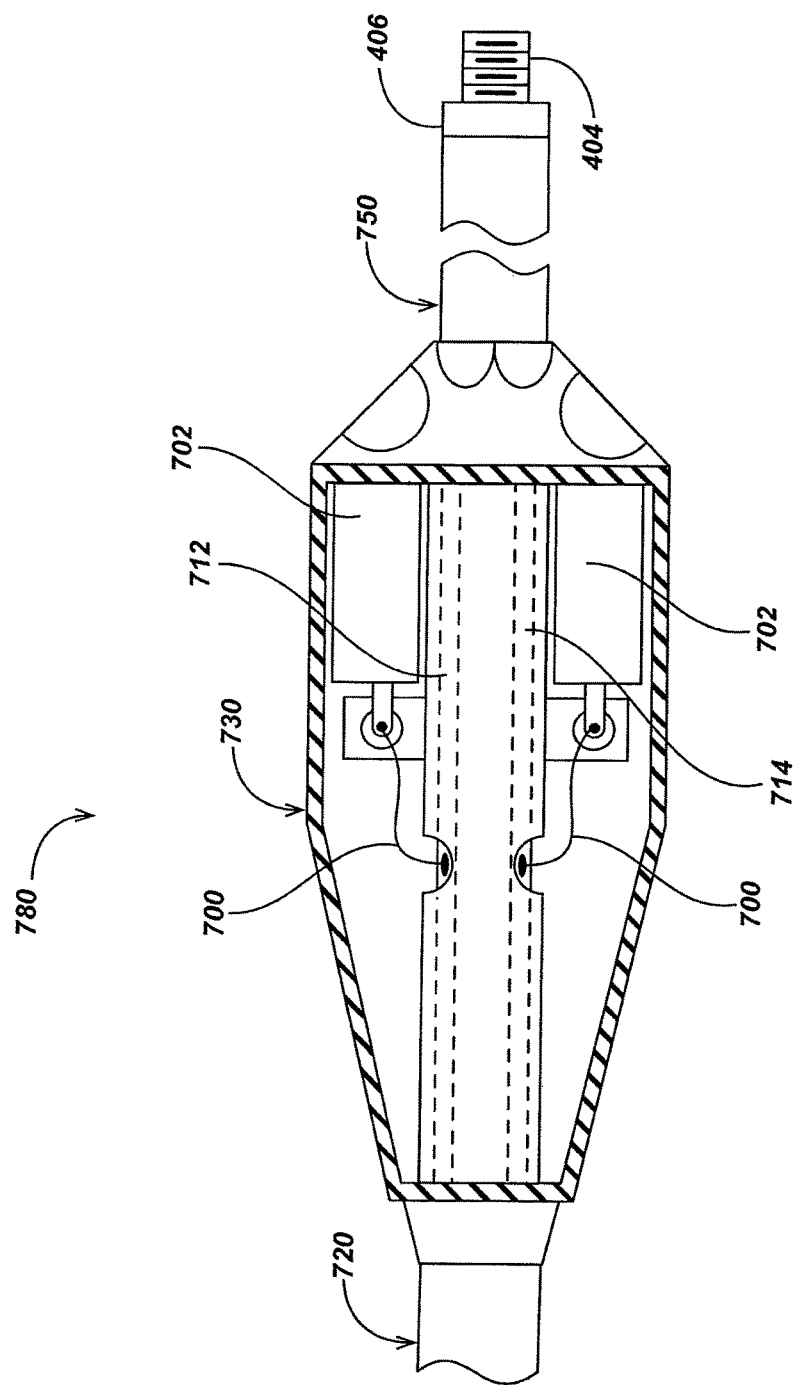
FIG. 7 is a side cutaway view of an embodiment of an effector end.

FIG. 7 illustrates a side cutaway view of details of an effector end embodiment 780, which may correspond with effector end 400 as shown in FIG. 4. In one embodiment, a camera assembly 730 is illustrated, which may correspond with camera assembly 108 as shown in FIG. 1 or other camera assemblies described previously herein. Outputs from camera assembly 730 may be coupled to one or more conductive wires 714 and/or one or more drain wires 712, which may correspond to conductive wires 214 and/or the drain wire 212 as shown in FIGS. 2 and 3, either directly or through a switching circuit (not shown).

Camera assembly 730 may be configured integrally with jetter push-cable 720, which may correspond with jetter push-cable 112 as shown in FIG. 1 and/or other push-cables described previously herein. Such an embodiment may include elements as illustrated previously herein, such as in FIGS. 2 and 3. For example, jetter push-cable 720 may have small openings cut into a nylon jacket corresponding to jacket 218, and through copper foil, such as copper foil 216, exposing the conductive wires 714 and/or the drain wire 712. In assembly, each of the conductive wires 714 may by exposed and soldered directly to a lead wire 700 in order to power a camera module 702 and/or provide a mechanism for data transfer.

In other embodiments, an IDC connector may be used to penetrate the surrounding layers of the conductive wires 714. Other mechanisms of connection to the conductive wires 714 as known or developed in the art may also be used to provide power and data connectivity to camera elements 702, which may correspond with camera elements described previously herein, as well as to other elements of camera assembly 730, such as switching circuits, lighting, and/or other components. For example, conductive wires 714 may be routed directly to the back of camera assembly 730 as shown in FIG. 7.

Figure 8:
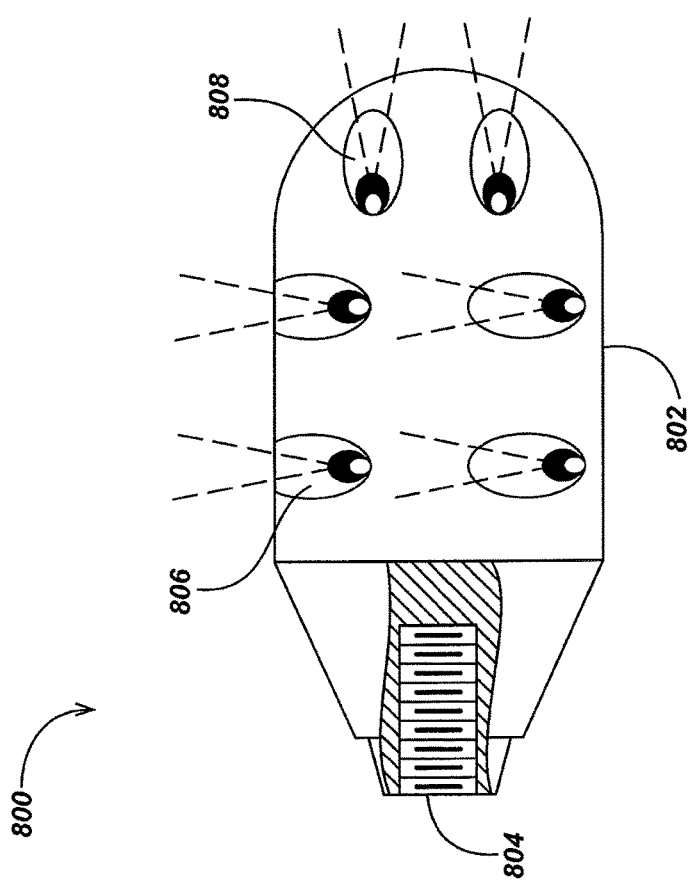
FIG. 8 is a perspective view of an embodiment of a jetter nozzle head.

Turning to FIG. 8, one embodiment of a jetter nozzle 800 is illustrated. Nozzle 800 may include a jetter nozzle head 802, which may include a jetter nozzle coupler 804 that may be formed to mate to a coupler end of a push-cable, such as coupler end 404 as shown in FIG. 4 or nozzle-side coupler 612 as shown in FIG. 6. Jetter nozzle coupler 804 may be configured to allow the jetter nozzle head 802 to rotate freely on bushings, bearings, or other rotational elements (not shown).

One or more lateral orifices 806 may be formed into jetter nozzle head 802 to allow pressurized fluid to be jetted from the jetter nozzle head 802 in pre-determined angles and directions at predefined output sizes. For example, the lateral orifices 806 may be sized and positioned to cause the jetter nozzle head 802 to spin, and may also be slanted slightly rearward to assist in propelling the jetter nozzle assembly 800 and an attached push-cable, such as push-cable 112 of FIG. 1, and/or other push-cables described previously herein, in a forward direction within the pipe under inspection. One or more forward-oriented orifices 808 may be included to enable an operator to clear debris or build-up. Jetter nozzle heads may be connected to a push-cable by the coupler end 404 as shown in FIG. 4, to the forward end of a hose element, such as hose 200 shown in FIG. 2 and/or to other hose elements described previously herein. Alternately, jetter nozzle heads may be connected to a push-cable by the coupler 606*a* as shown in FIG. 6.

Figure 9:
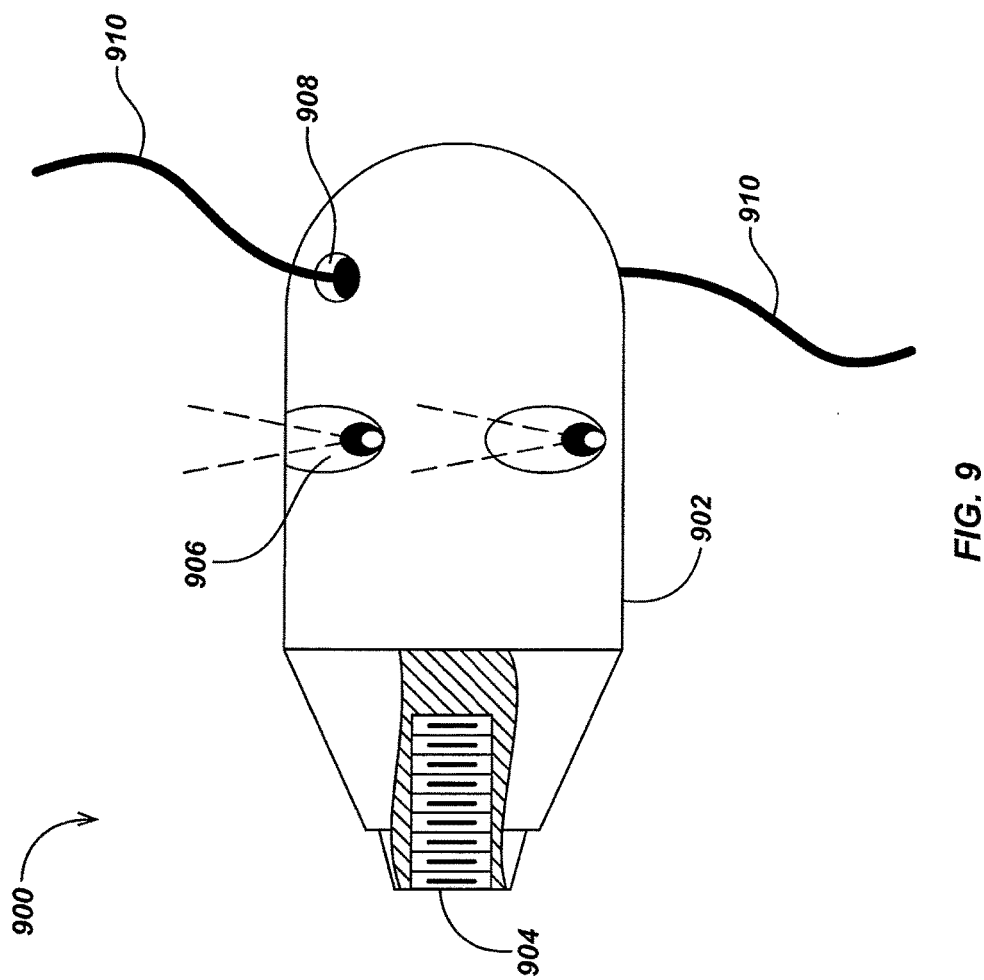
FIG. 9 is a perspective view of an embodiment of a cutter-line jetter nozzle head.

An embodiment of a cutter-line jetter nozzle head 900 is illustrated in FIG. 9. Head 900 may include a cutter-line jetter nozzle body 902 having a base coupler 904, which may correspond to the jetter nozzle coupler 804 as shown in FIG. 8. Head 900 may further include a series of lateral jet orifices 906. A special purpose port 908 into which lengths of a cutter line 910 that may be composed of a cutting material such as a high-density synthetic material or stainless steel, for example, may also be disposed in the front of the cutter-line jetter nozzle head 900. The lateral jet orifices 906 may be used to rotate the cutter line 910 using pressurized fluid. Other embodiments may include attachment points for cutter blades and/or other obstruction clearance tools, for example. Such a configuration enables an operator to quickly remove or attach an array of different jetter nozzles and/or cutters, and/or other obstruction clearage devices according to the requirements of the specific application.

Figure 10:
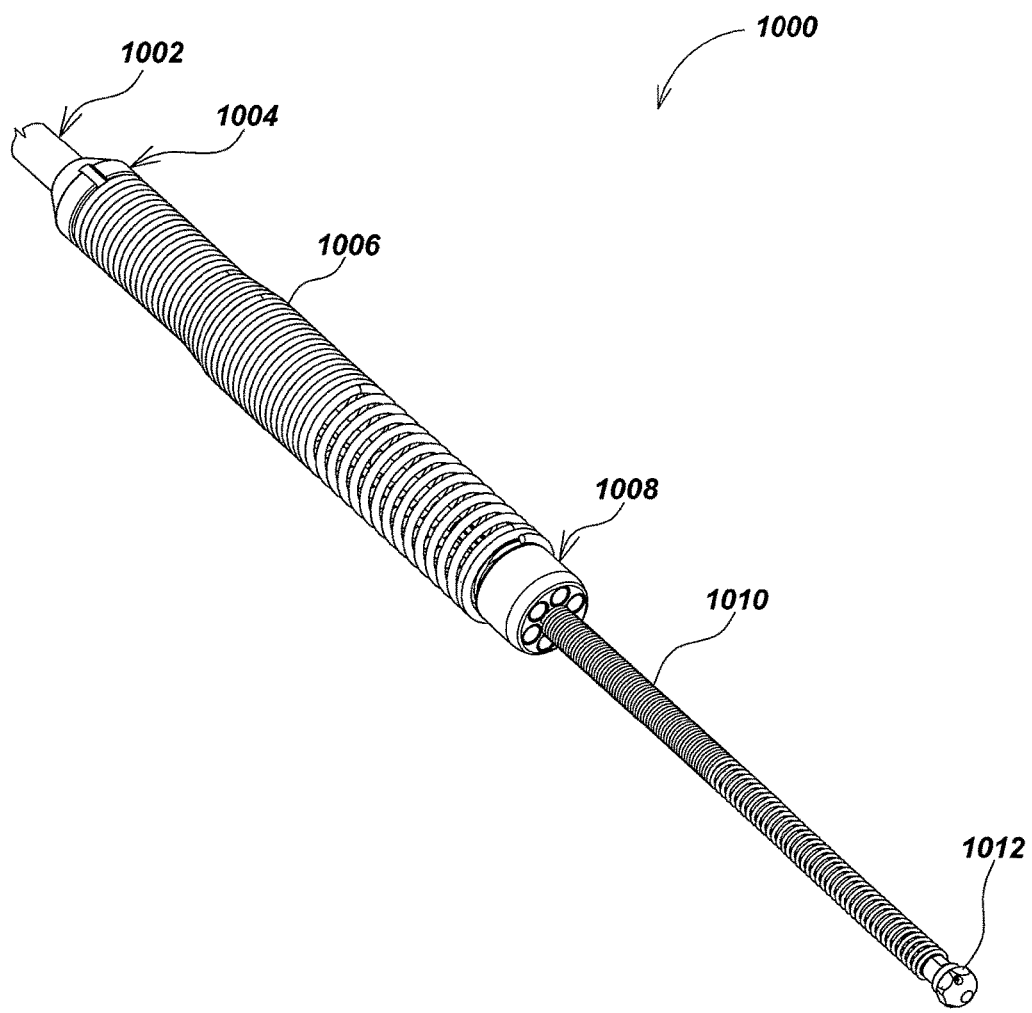
FIG. 10 is an isometric view of an embodiment of an alternative pipe inspection pushjetter.

FIG. 10 illustrates an alternative embodiment of details of a pipe inspection pushjetter 1000. Various details of the illustrated embodiment of pushjetter 1000 may be used in an obstruction clearance system such as system 100 of FIG. 1. Pushjetter 1000 may include a jetter push-cable 1002 that connects to an end adaptor 1004. A posterior spring 1006 may be used to connect an end adaptor 1004 to a camera and light module 1008. An anterior spring 1010 extends centrally from the center of the camera and light module 1008 to a pushjetter nozzle 1012. The posterior spring 1006 and the anterior spring 1010 may be used to provide additional stiffness and protection for internal components (not shown).

Figure 11:
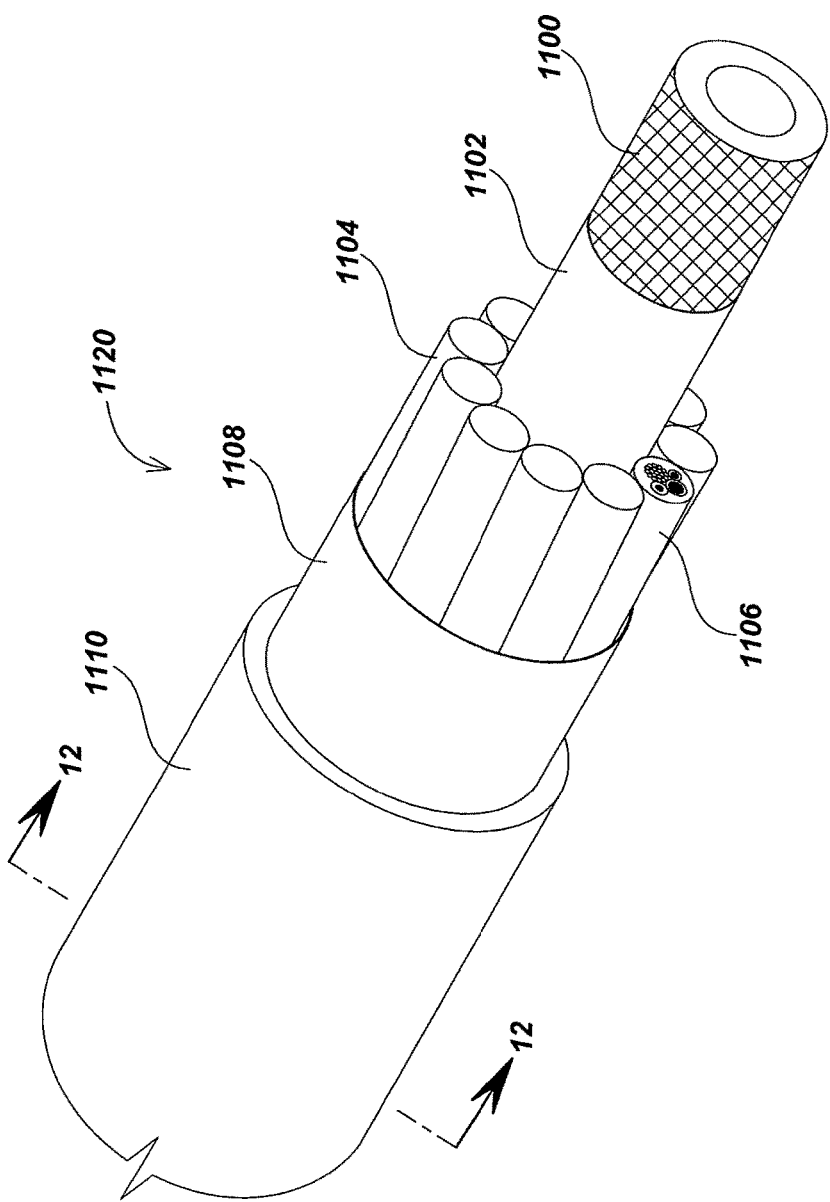
FIG. 11 is an enlarged fragmentary isometric view of an embodiment of an alternative jetter push-cable.

FIG. 11 illustrates additional details of an alternative jetter push-cable 1120, which may correspond to alternative jetter push-cable 1002 as shown in FIG. 10. Push-cable 1120 may include a reinforced hose 1100, such as a stainless steel braided hose, and may be optionally surrounded by a low friction layer 1102, which may be composed of material such as Teflon® or other low friction materials. The low friction layer 1102 may be surrounded by a series of rods 1104, which may be fiberglass rods or rods of other low weight, high strength materials. A composite cable 1106, which may include multiple conductors suitable for conveyance of power, signals, and/or a ground wire, which may further serve as a strengthening member, may be included. A foil layer 1108, which may be configured to provide shielding, may optionally surround the rods 1104 and the composite cable 1106. An outer layer 1110 configured for durability and ease of deployment, such as of a material such as nylon, may be used to surround the shield foil layer 1108 and inner layers.

Figure 12:
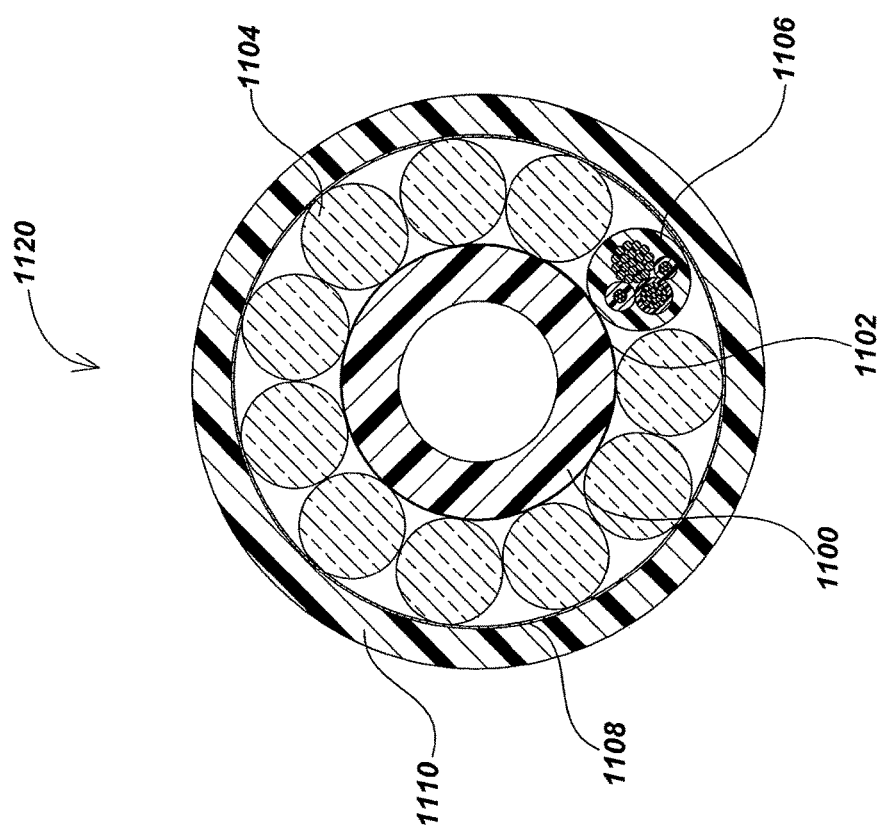
FIG. 12 is an end-view of the alternative jetter push-cable embodiment shown in FIG. 11.

FIG. 12 illustrates an end or cross-sectional view of various layers of the push-cable embodiment 1120 of FIG. 11. The composite cable 1106 may provide wiring for powering and transmitting information for the alternative pipe inspection pushjetter 1000 as shown in FIG. 10.

Figure 13:
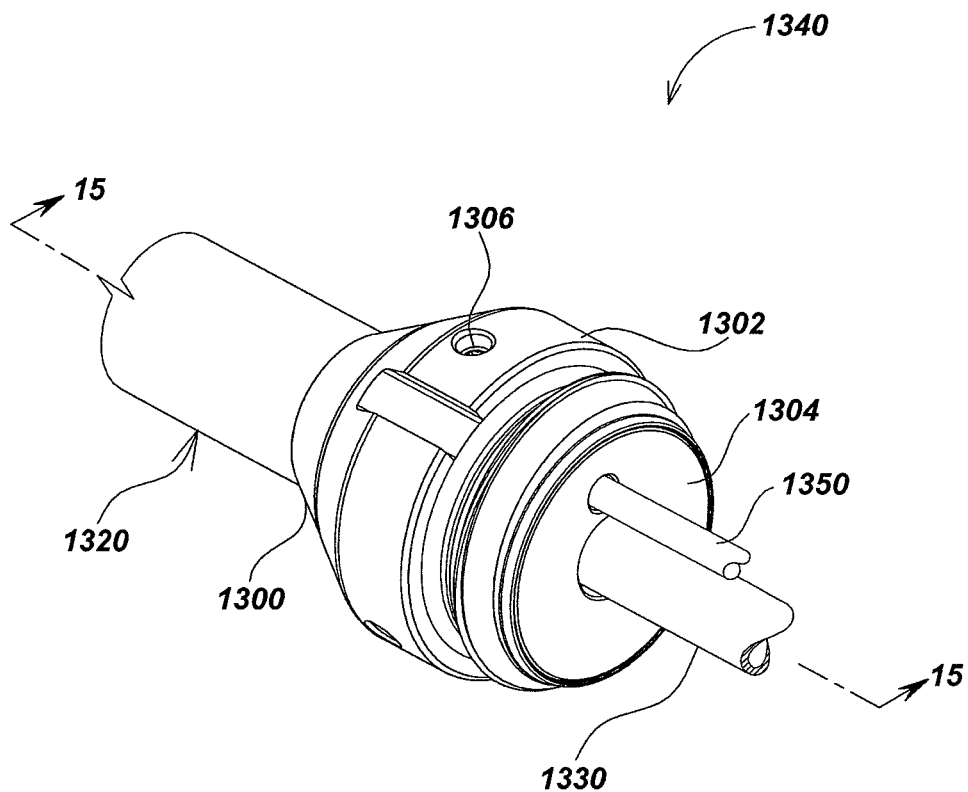
FIG. 13 is an isometric view of the alternative jetter push-cable embodiment shown in FIG. 11, with an end adaptor.

Referring to FIG. 13, an end adaptor 1340, which may correspond to end adaptor 1004 shown in FIG. 10, may externally include a termination housing 1300, a spring shell 1302, and a termination cap 1304. The termination housing 1300 and the termination cap 1304 may be threaded to mate together. The spring shell 1302 may be sized to mount around the termination housing 1300 and the termination cap 1304, and may be secured thereto by a plurality of set screws 1306 that screw into the sides of the spring shell 1302. End adaptor 1340 may be coupled to a push-cable 1320, which may correspond with push-cable 1002 as shown in FIG. 10. Similarly a composite cable 1350, which may correspond with cable 1106 of FIG. 10, and/or a shield 1330, which may correspond with shield 1108, may be included as shown.

Figure 14:
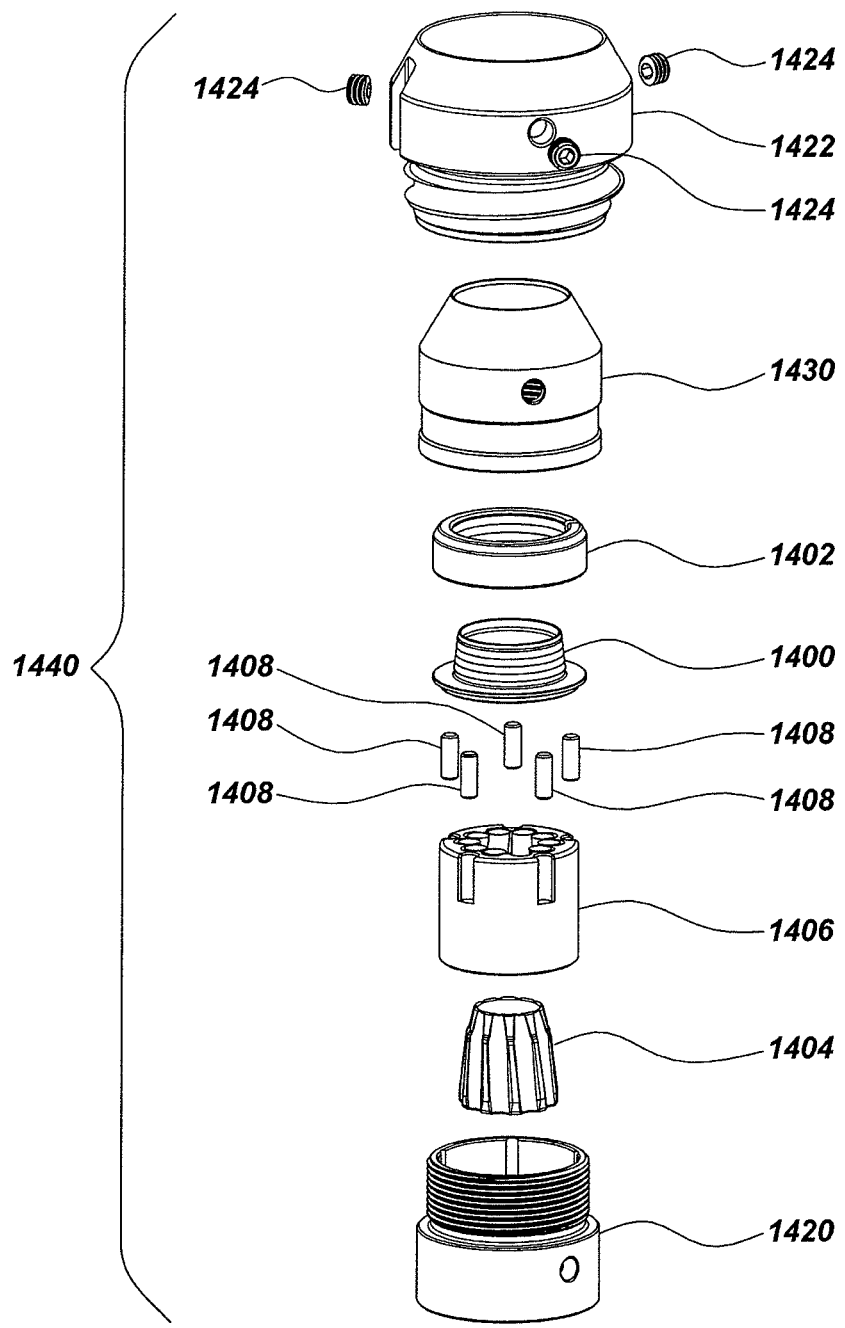
FIG. 14 is an exploded view of the end adaptor embodiment shown in FIG. 13.

FIG. 14 illustrates additional details of an end adaptor 1440, which may correspond to end adaptor 1004 as shown in FIG. 10, and/or other end adaptors described previously herein. End adaptor 1440 may include an inner jacket wedge 1400, an outer jacket wedge 1402, an inner rod wedge 1404, and an outer rod wedge 1406 with a series of dowel pins 1408. The inner jacket wedge 1400 and the outer jacket wedge 1402 may be shaped so that the end of the inner jacket wedge 1400 may be secured into the outer jacket wedge 1402.

In assembly, as an alternative jetter push-cable such as cable 1002 (not shown) enters the end adaptor 1440, an outer layer, such as layer 1110 as shown in FIG. 11 may be peeled back and secured between the inner jacket wedge 1400 and the outer jacket wedge 1402. A reinforced hose, such as hose 1100 as shown in FIG. 11, may continue through the center of the inner jacket wedge 1400. The inner rod wedge 1404 may be constructed to fit within the outer rod wedge 1406. Grooves may be formed along the outer surface of the inner rod wedge 1404 as well as the inner surface of the outer rod wedge 1406. The grooves may be constructed to accommodate rods (not shown), such as rods 1104 of FIG. 11, a composite cable (not shown), such as cable 1106, to separate the rods and composite cable from a low friction layer (not shown), such as layer 1102 and a reinforced hose (not shown), such as hose 1100.

In assembly, the fiberglass rods (not shown) may be trimmed off at the forward facing edge of the outer rod wedge 1406 while the composite cable (not shown) may be fed through a hole on the forward face of the termination cap 1404, which may correspond with the termination cap 1304 shown in FIG. 13. The reinforced hose (not shown) may continue through the center of the inner rod wedge 1404 and a centrally located hole formed through the forward face of the termination cap 1420. A spring shell 1422, which may correspond with the spring shell 1302 as shown in FIG. 13, may be further formed with a series of grooves to accommodate the end of a posterior spring (not shown), such as spring 1006 of FIG. 10. The spring shell 1422 may mount by a plurality of set screws 1424, which may correspond with the set screws 1306 as shown in FIG. 13, that screw into the sides of the spring shell 1422 A termination housing 1430, which may correspond with housing 1300 of FIG. 13, may be included as shown.

Figure 15:
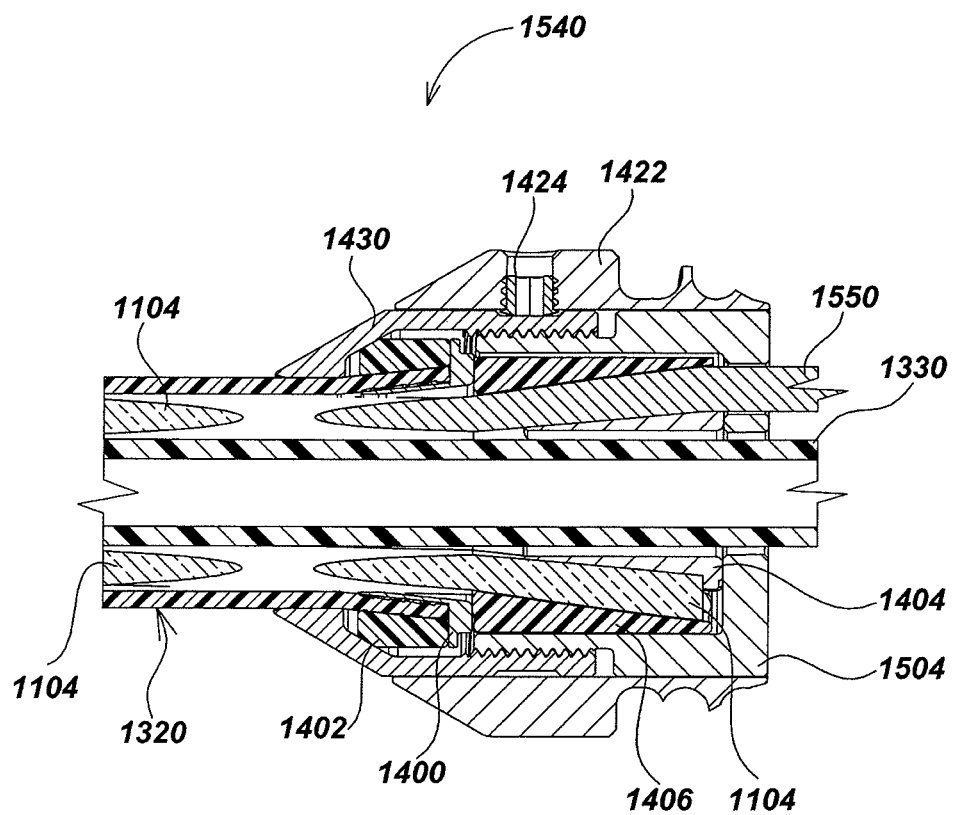
FIG. 15 is a sectional view of the alternate jetter push-cable embodiment along line 15-15 as shown in FIG. 13.

FIG. 15 illustrates a cutaway view of an embodiment of an end adaptor 1540, which may correspond to end adaptor 1004 of FIG. 10 and/or other end adaptors described previously herein. The cutaway view shown in FIG. 15 may correspond with line 15-15 as shown in FIG. 13 with corresponding elements. A composite cable 1550, which may correspond with composite cable 1106 of FIG. 11, may be configured as shown to pass through a hole on the forward face of termination cap 1504, which may correspond with termination cap 1304 of FIG. 13.

Figure 16:
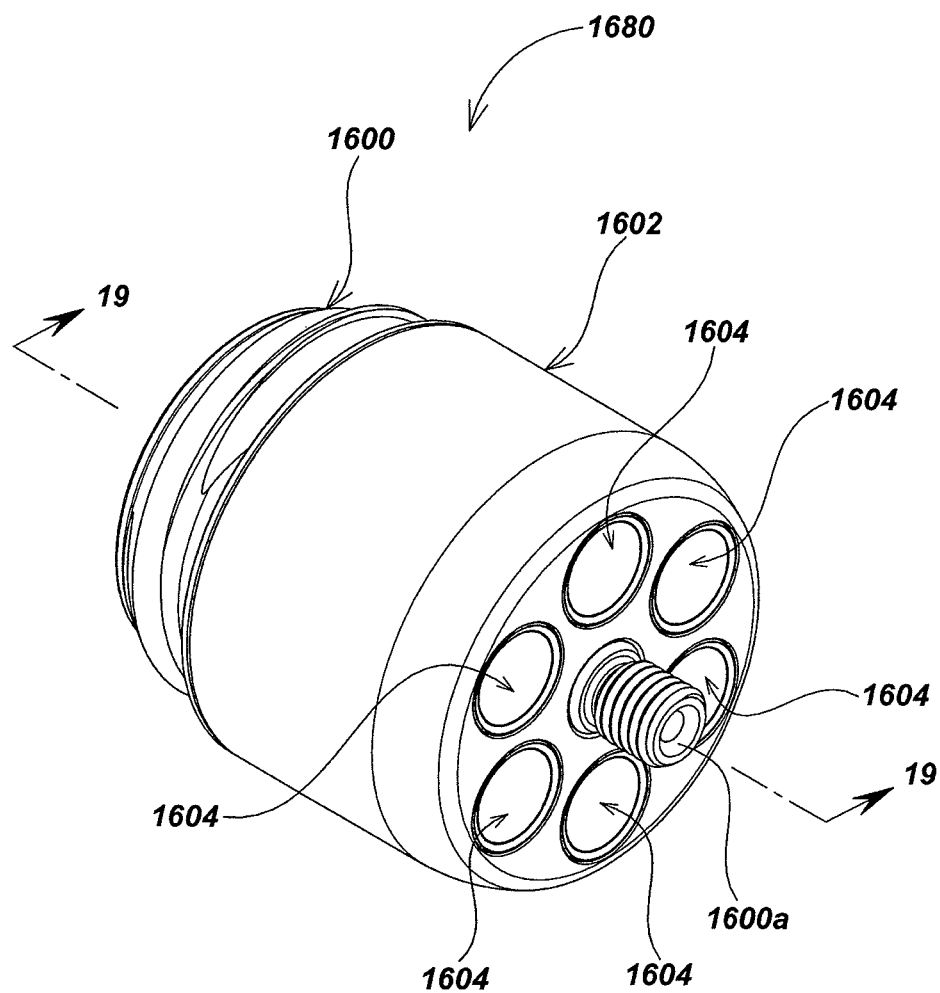
FIG. 16 is an isometric view of an embodiment of a camera and light module.

Referring to FIG. 16, an embodiment of a camera and light module 1680, which may correspond to camera and light module 1008 as shown in FIG. 10 is illustrated. Module 1680 may include a rear housing 1600 and a front bezel piece 1602. The rear housing 1600 and the front bezel piece 1602 may be formed so that they may be secured together in such a way that a central hollow post 1600a with threaded ends formed on the rear housing 1600, fits through a circular opening on the front bezel piece 1602. A series of window modules 1604, such as lens/LED window modules, may be secured within the forward face of the front bezel piece 1602.

Figure 17:
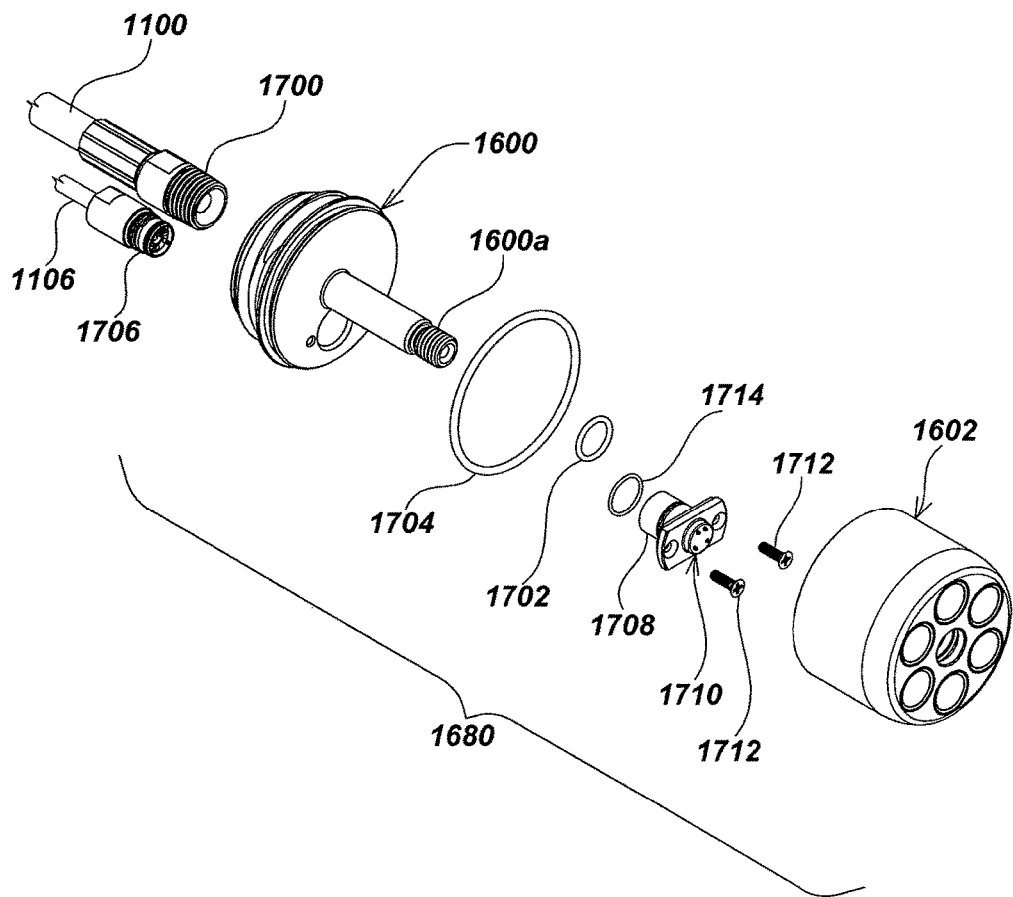
FIG. 17 is an exploded view of an embodiment of a camera and light module, a single cable, and a reinforced hose.

FIG. 17 illustrates additional details associated with the embodiment of module 1680 of FIG. 16. A reinforced hose, such as hose 1100 of FIG. 11 and/or other hoses described previously herein, may be secured to a threaded hose fitting 1700 and threaded into the back of rear housing 1600 during assembly. The reinforced hose 1100 and central hollow post 1600a of the rear housing 1600 may be aligned such that pressurized fluid may flow from the reinforced hose and through the central hollow post 1600a of the rear housing 1600. A central bezel piece O-ring 1702 may be used to aid in providing a waterproof seal between the central hollow post 1600a and the front bezel piece 1602. A rear housing O-ring 1704 may be used to aid in further providing a waterproof seal between the rear housing 1600 and the front bezel piece 1602.

A cable connector 1706 may be fitted onto the end of a composite cable, such as cable 1106 of FIG. 11 and/or other composite cables described previously herein. A connector sleeve 1708 may be fitted within an offset hole formed on the rear housing 1600. A pin connector 1710 may be secured to the connector sleeve 1708 and the rear housing 1600 by a set of small screws 1712. In assembly, the cable connector 1706 may be plugged into the connector sleeve 1708 and the pin connector 1710 attached to the rear housing 1600. A sleeve O-ring 1714 may be used to aid in providing a waterproof seal between the connector sleeve 1708 and the rear housing 1600.

Figure 18:
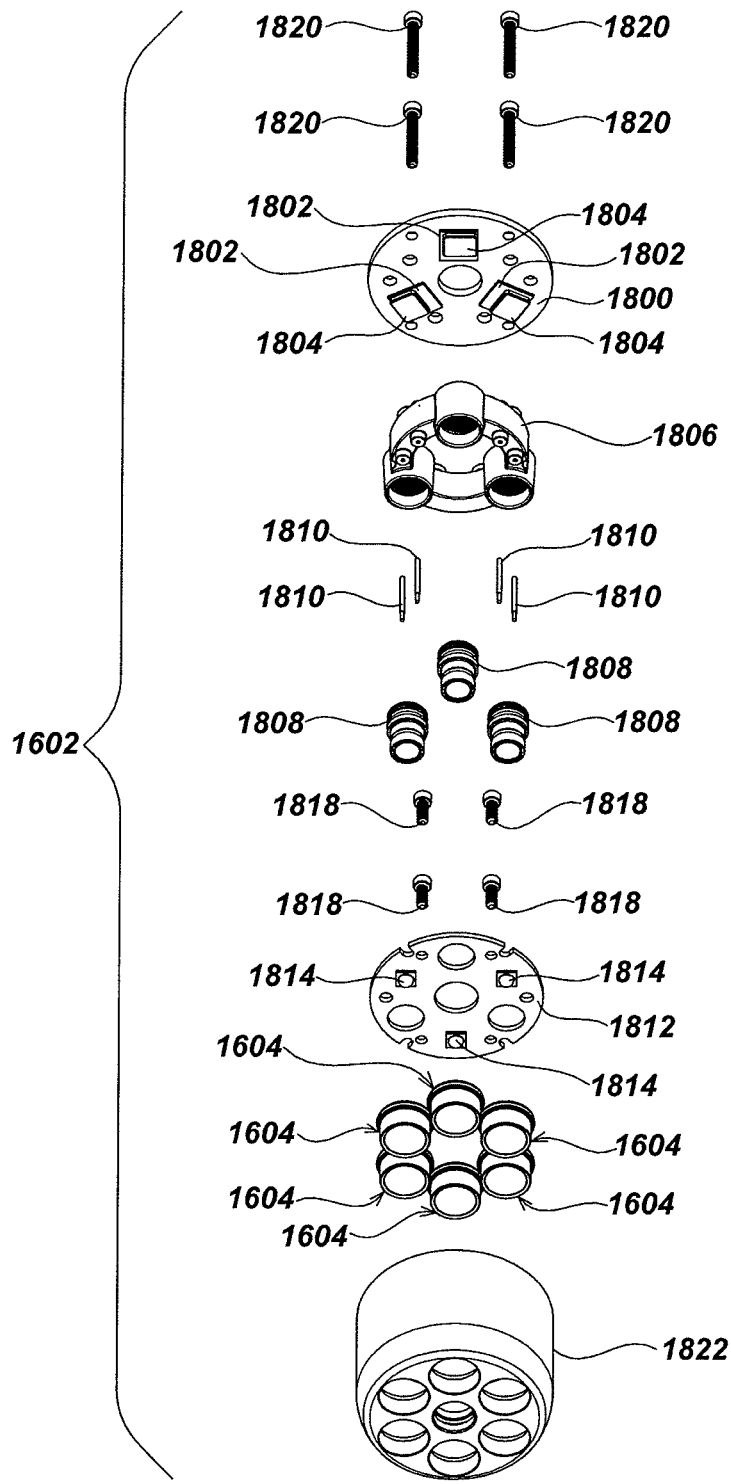
FIG. 18 is an exploded view of the front bezel piece embodiment of the camera and light module embodiment shown in FIG. 16.

FIG. 18 illustrates additional details of an embodiment of camera assembly and bezel 1602 of FIG. 16. A pin connector 1710 as shown in FIG. 17 creates a mechanism by which the pins of cable connector 1706 may be aligned with contact pads on the side of a camera printed circuit board (PCB) 1800 opposite a series of image sensors 1802. The camera PCB may include switching circuits such as described previously herein, as well as other circuits associated with camera and lighting element operation. Camera PCB 1800 may be annular in shape so as to allow the central hollow post 1600a of the rear housing 1600 to pass through the center of the camera PCB 1800.

One suitable camera element is the Omnivision OV7962 sensor. Sensor OV7962, or another imaging sensor, may be used as image sensor 1802 and/or as a camera element as described previously herein. Multiple image sensors 1802 may be evenly spaced on the camera PCB 1800. In an exemplary embodiment, three image sensors 1802 may be used on the camera PCB 1800. An IR filter 1804 may also be secured in front of each of the image sensors 1802.

A camera holder ring and lens mount 1806, which may also be annular in shape, may be used to hold in place a series of lens modules 1808 in front of the image sensors 1802 and the IR filters 1804 on the camera PCB 1800. The lens modules 1808 may be comprised of a series of lenses and O-rings secured together within a largely cylindrical housing. A series of electrical spring contacts 1810 may be secured within the camera holder ring and lens mount 1806 in order to power lighting elements, which may be mounted on an LED PCB 1812.

The LED PCB 1812 may also be annular in shape with holes formed to allow multiple lens modules 1808 to pass through in assembly. Between each of the holes on the LED PCB 1812 where the lens modules 1808 are made to pass though, an LED 1814 may be connected to the LED PCB 1812. One of the lens/LED window modules 1604 may be secured above each of the lens modules 1808 and the LEDs 1814. A series of short screws 1818 may be used to secure the LED PCB 1812 to the front bezel piece 1602. A series of long screws 1820 may be further used to secure the camera PCB 1800, the camera holder ring and lens mount 1806, and the lens modules 1808 to the LED PCB 1812 and a bezel casing 1822.

Figure 19:
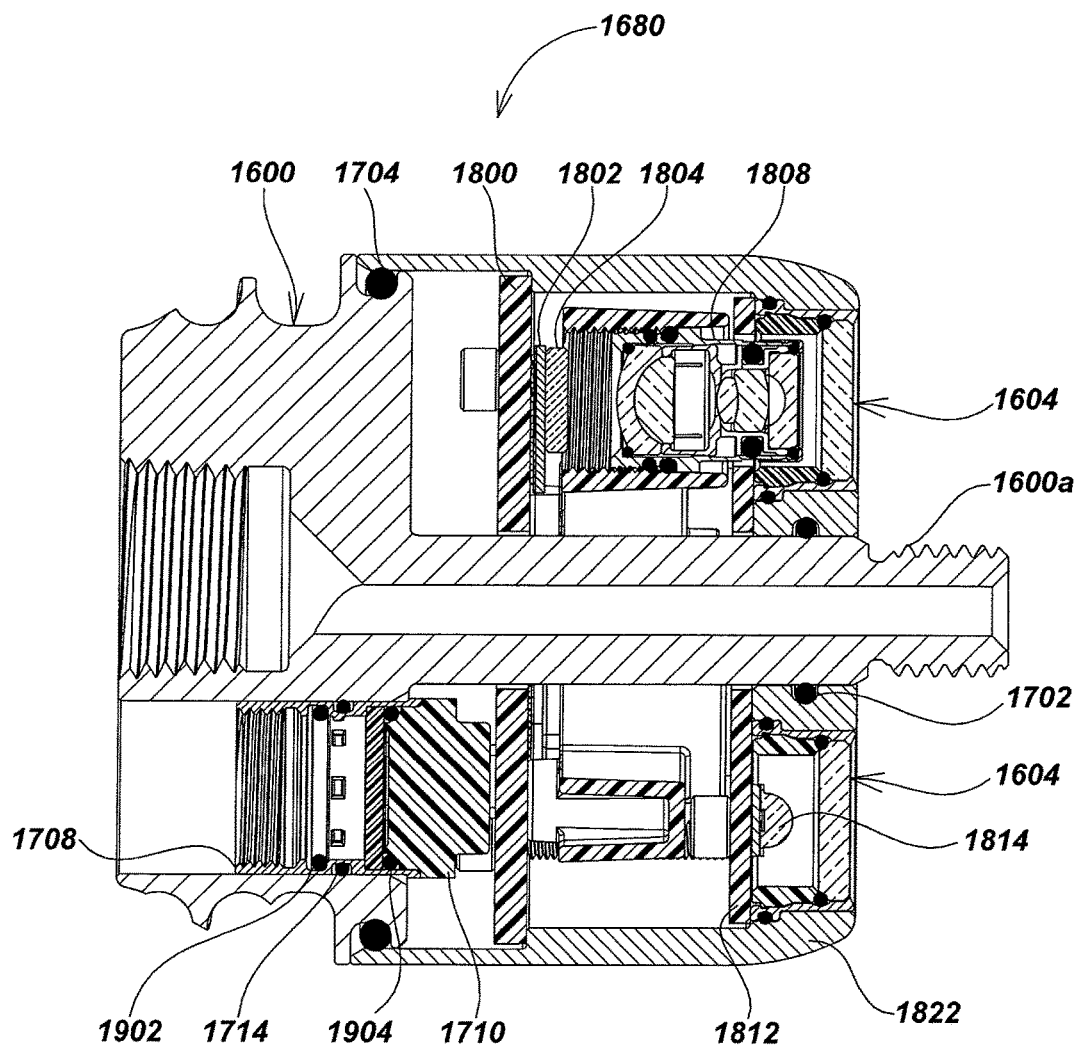
FIG. 19 is a sectional view of the camera and light module embodiment along line 19-19 as shown in FIG. 16.

Referring to FIG. 19, a sectional view along line 19-19 of FIG. 16 further shows details of an embodiment of assembly of the camera and light module 1680, which may correspond to the camera and light module 1008 as shown in FIG. 10. A cable connector O-ring 1902 may be used to aid in providing a waterproof seal between the cable connector 1706 of FIG. 17 and the connector sleeve 1708. A pin connector O-ring 1904 may be secured between the connector sleeve 1708 and the pin connector 1710.

Still referring to FIG. 19, in some alternative embodiments, the lens/LED window modules 1604, the lens modules 1808, the IR filters 1804 and/or the image sensors 1802 may be oriented in a number of different ways. For instance, these components may be divergent from the central axis of the camera and light module 1680 at angles of different degrees providing a different view of the inspection area, or a different number of individual camera modules and light modules may be used. In addition, a position sensing device (not illustrated), such as a multi-axis accelerometer, may be used to detect the orientation of each of the image sensors 1802 and provide a signal for use by a switching circuit (not shown) to select a particular image or video to display to the user. The particular image or video may include, for example, a composite display from several of the image sensors 1802, separate displays from each of the image sensors 1802, or a single display from one of the image sensors 1802 (such as a top-oriented image). In other embodiments, the image sensors 1802 may be manually selected by the user, such as in response to a received user input at a switching circuit.

Figure 20:
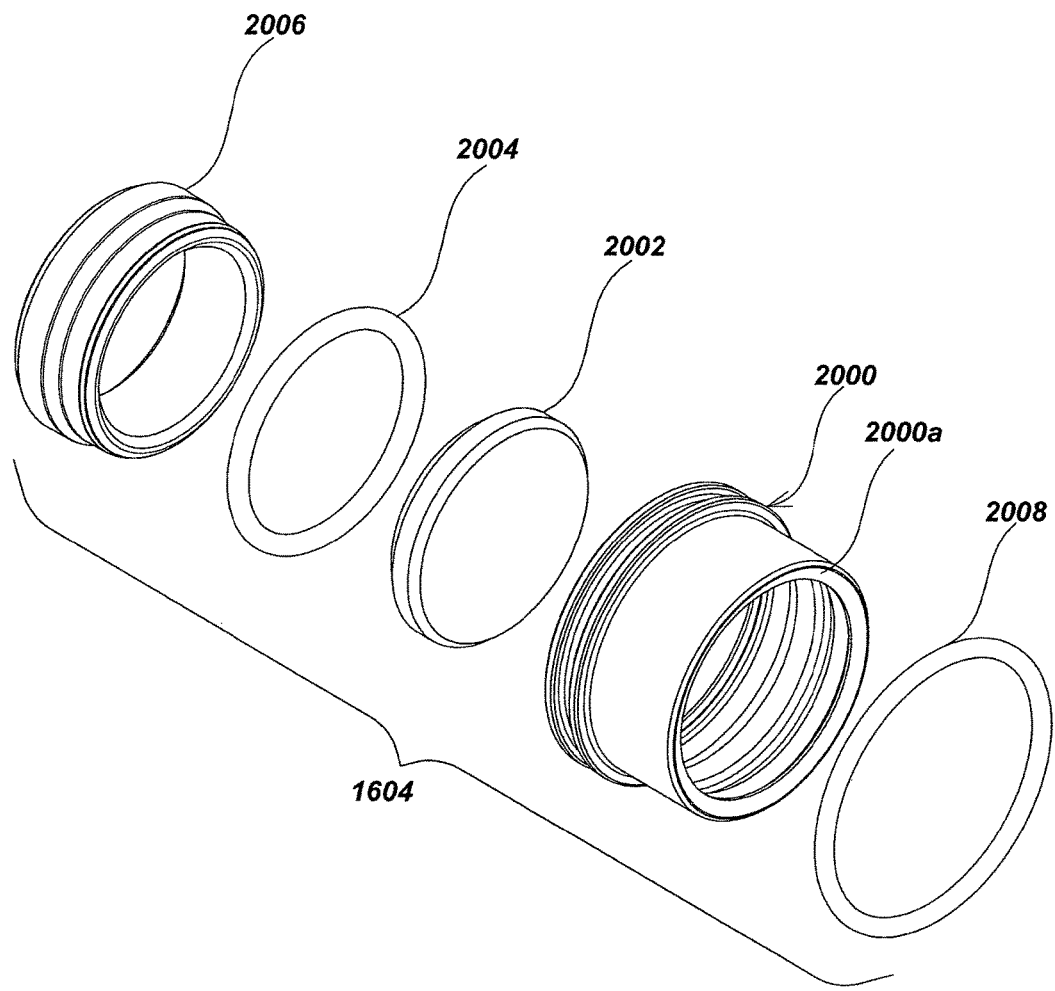
FIG. 20 is an exploded view of an embodiment of a lens/LED window module.

FIG. 20 illustrates additional details of embodiments of the window modules 1604 of FIG. 16. Window modules 1604 may be formed by a window seat 2000 that may be largely cylindrical in shape with a front lip 2000a of smaller diameter formed on the forward facing side of the window seat 2000 so that a sapphire window 2002 may fit within the window seat 2000 and be secured behind the front lip 2000a. An inner window O-ring 2004 may be inserted behind the sapphire window 2002 and secured by a window press ring 2006. The lens/LED window module 1604 may also contain an outer window O-ring 2008 fitted on the outside of the window seat 2000 to create a waterproof seal between the window seat 2000 and the front bezel piece 1602 as shown in FIG. 16.

Figure 21:
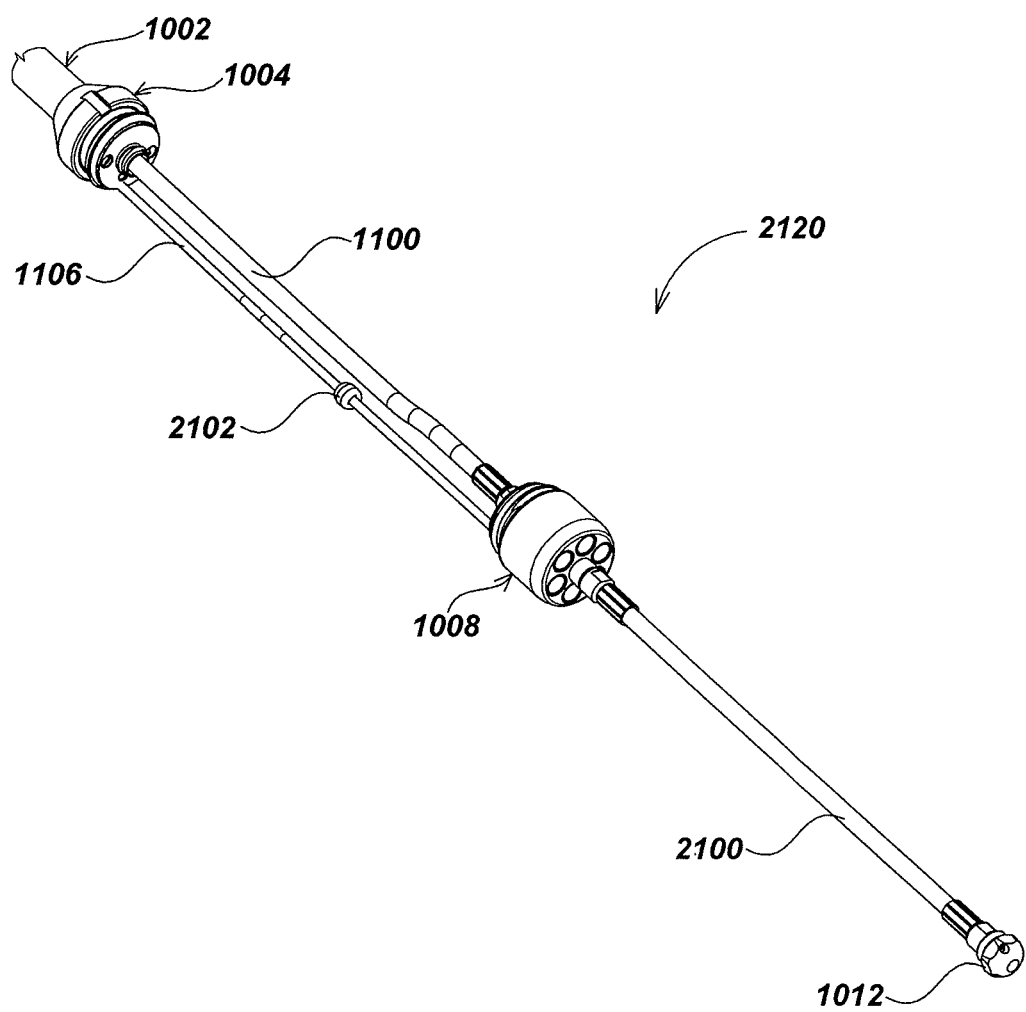
FIG. 21 is an isometric view of the alternative pipe inspection pushjetter embodiment shown in FIG. 10, with a large spring and a small spring removed.

Referring to FIG. 21, alternative pipe inspection pushjetter embodiment 1000 of FIG. 10 is shown with posterior spring 1006 and anterior spring 1010 removed. When the anterior spring 1010 is removed, an extender piece 2100 may be better seen. The extender piece 2100 may be used to connect the central hollow post 1600a of FIG. 16 of the rear housing 1600 from the camera and light module 1680, which may correspond to the camera and light modules shown in FIGS. 10, 16, and 19, to a pushjetter nozzle, such as pushjetter nozzle 1012 or other pushjetter nozzles shown previously herein. A sonde 2102 may optionally be connected to the alternative pipe inspection pushjetter 1000 to aid the user in locating work areas that may be buried within the ground.

In FIG. 21, the sonde 2102 may be located on a composite cable, such as composite cable 1106 or other composite cables described previously herein, between an end adaptor, which may also correspond to end adaptor 1004 or other end adaptors as shown in FIGS. 10, 11, 12, 13, 14, and 15, and a camera and light module, such as module 1008 and/or other camera and light modules described previously herein. In some alternative embodiments, the sonde 2102 may be built into other areas such as within a camera and light module such as camera and light module 1008 and/or other camera assembly or camera and light modules described previously herein.

In some configurations, the apparatus and systems described herein may include means for implementing features or providing functions described herein. In one aspect, the aforementioned means may be a module including a processor or processors, associated memory and/or other electronics in which embodiments of the invention reside, such as to implement image and/or video signal processing, switching, transmission, or other functions to process and/or condition camera outputs, control lighting elements, control camera selection, or provide other electronic or optical functions described herein. These may be, for example, modules or apparatus residing in camera assemblies, camera and lighting assemblies, or other assemblies disposed on or within a push-cable or similar apparatus.

In one or more exemplary embodiments, the electronic functions, methods and processes described herein and associated with camera and lighting elements may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

As used herein, computer program products comprising computer-readable media include all forms of computer-readable medium except, to the extent that such media is deemed to be non-statutory, transitory propagating signals.

It is understood that the specific order or hierarchy of steps or stages in the processes and methods disclosed herein are examples of exemplary approaches. Based upon design preferences, it is understood that the specific order or hierarchy of steps in the processes may be rearranged while remaining within the scope of the present disclosure.

Those of skill in the art would understand that information and signals, such as video and/or audio signals or data, control signals, or other signals or data may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, electromechanical components, or combinations thereof. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative functions and circuits described in connection with the embodiments disclosed herein with respect to camera and lighting elements may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The disclosure is not intended to be limited to the aspects shown herein, but is to be accorded the full scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use embodiments of the present invention. Various modifications to these aspects will be readily apparent to those skilled in the art, and the generic principles defined herein may be applied to other aspects without departing from the spirit or scope of the invention. Thus, the invention is not intended to be limited to the aspects shown herein but is to be accorded the widest scope consistent with the principles and novel features disclosed herein. It is intended that the following Claims and their equivalents define the scope of presently claimed invention.

The invention claimed is:

1. A jetting system for clearing pipe obstructions, comprising:
   a pump unit for providing pressurized fluid;
   a push-cable, coupled to the pump unit, receiving the pressure fluid from the pump unit, the push cable comprising a hose having a channel to transmit the pressurized fluid therethrough; and
   a jetter head coupled to a distal end of the push-cable, the jetter head including:
   a jetter nozzle having one or more orifices through which the pressurized fluid is expelled to clear a pipe or cavity; and
   one or more cutting elements disposed on or within the jetter nozzle, wherein the cutting elements are rotatable by the pressurized fluid to clear obstructions in the pipe or cavity.

2. The system of claim 1, further comprising a camera assembly including a plurality of imaging elements arranged in an annular configuration around or within the push-cable.

3. The system of claim 2, wherein the camera assembly further including one or more sensors to sense orientation of the imaging elements and orientation of the push-cable within the pipe or cavity.

4. The system of claim 3, wherein the one or more sensors include a multiaxis accelerometer.

5. The system of claim 3, wherein the imaging elements are automatically controlled based on orientation of the push-cable within the pipe or cavity.

6. The system of claim 1, further comprising a stiffening structure helically wrapped around the hose to provide rigidity to the push-cable.

7. The system of claim 6, wherein the stiffening structure comprises a plurality of rods.

8. The system of claim 1, wherein the hose comprises a thermoplastic material.

9. The system of claim 1, further comprising a reinforcing braid disposed around the hose.

10. The system of claim 2, further comprising one or more lighting elements disposed in the camera assembly.

11. The system of claim 10, wherein the one or more lighting elements comprise LEDs.

12. The system of claim 1, wherein the one or more orifices comprise a plurality of orifices arranged and positioned to spin the jetter nozzle in response to jetting of the pressurized fluid.

13. The system of claim 1, wherein the cutting elements include flexible cutting strands or blades.

14. The system of claim 13, wherein the cutting strands or blades comprises a high-density synthetic material or a stainless steel.

15. A system for inspecting pipes and clearing pipe obstructions, comprising:
    a pump unit for providing pressurized fluid;
    a push-cable, coupled to the pump unit, receiving the pressure fluid from the pump unit, the push cable comprising a hose having a channel to transmit the pressurized fluid therethrough;

a jetter nozzle coupled to a distal end of the push-cable, the jetter nozzle configured to control a flow of the pressurized fluid from the distal end of the push-cable, wherein the jetter nozzle includes one or more orifices; and a camera assembly mounted on or within a segment of the push-cable, the camera assembly includes one or more imaging elements.

16. The system of claim 15, wherein the imaging elements are arranged in an annular configuration around or within the segment of the push-cable.

17. The system of claim 15, further comprising one or more lighting elements disposed in the camera assembly.

18. The system of claim 17, wherein the one or more lighting elements comprise LEDs.

19. The system of claim 15, further comprising a stiffening structure helically wrapped around the hose, wherein the stiffening structure comprises a plurality of rods.

20. The system of claim 15, further comprising a reinforcing braid disposed around the hose.

* * * * *